(12) United States Patent
Iwasaki et al.

(10) Patent No.: US 9,996,151 B2
(45) Date of Patent: Jun. 12, 2018

(54) DETECTING EYE MOVEMENT BASED ON A WEARABLE DETECTION APPARATUS

(71) Applicant: SONY CORPORATION, Tokyo (JP)

(72) Inventors: Masanori Iwasaki, Kanagawa (JP); Yoichiro Sako, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days. days.

(21) Appl. No.: 14/902,953

(22) PCT Filed: Jul. 8, 2014

(86) PCT No.: PCT/JP2014/068126
§ 371 (c)(1),
(2) Date: Jan. 5, 2016

(87) PCT Pub. No.: WO2015/008654
PCT Pub. Date: Jan. 22, 2015

(65) Prior Publication Data
US 2016/0147301 A1    May 26, 2016

(30) Foreign Application Priority Data

Jul. 19, 2013   (JP) ................................ 2013-150433

(51) Int. Cl.
*A61B 5/00* (2006.01)
*G06F 3/01* (2006.01)
(Continued)

(52) U.S. Cl.
CPC .............. *G06F 3/013* (2013.01); *A61B 3/113* (2013.01); *G06F 1/163* (2013.01); *G06F 3/0325* (2013.01);
(Continued)

(58) Field of Classification Search
None
See application file for complete search history.

(56) References Cited

U.S. PATENT DOCUMENTS

| 2002/0024631 A1* | 2/2002 | Roffman | G02C 7/04 351/159.1 |
| 2006/0119794 A1* | 6/2006 | Hillis | G02B 3/14 351/205 |

(Continued)

FOREIGN PATENT DOCUMENTS

WO    02/067688 A1    9/2002

OTHER PUBLICATIONS

Extended European Search Report of EP Patent Application No. 14826483.1, dated Feb. 27, 2017, 08 pages.

*Primary Examiner* — Jennifer Mehmood
*Assistant Examiner* — Carl Adams
(74) *Attorney, Agent, or Firm* — Chip Law Group

(57) ABSTRACT

A contact lens type line-of-sight detection apparatus has a shape such that it is wearable on an eyeball of a user. Furthermore, in the line-of-sight detection apparatus, a plurality of light-emitting sections that output light and a plurality of light-receiving elements that receive light reflected by an eyeball surface. The light-receiving elements receive light that has been output from the light-emitting sections and reflected by the eyeball surface and output light-receiving signals according to amounts of light received. The signal processing unit detects a line of sight of the user based on the light-receiving signals of the light-receiving elements. The present technology can be applied to a contact lens type line-of-sight detection apparatus or a display apparatus.

19 Claims, 20 Drawing Sheets

(51) Int. Cl.
*A61B 3/113* (2006.01)
*G06F 1/16* (2006.01)
*G06F 3/03* (2006.01)
*G06K 9/00* (2006.01)
*G02B 27/01* (2006.01)
*A61B 5/024* (2006.01)

(52) U.S. Cl.
CPC ...... G06K 9/00604 (2013.01); *A61B 5/02416* (2013.01); *A61B 5/6821* (2013.01); *G02B 2027/0187* (2013.01)

(56) References Cited

U.S. PATENT DOCUMENTS

| | | | |
|---|---|---|---|
| 2006/0227067 A1 | 10/2006 | Iwasaki | |
| 2009/0189974 A1 | 7/2009 | Deering | |
| 2010/0001926 A1 | 1/2010 | Amirparviz et al. | |
| 2013/0021373 A1* | 1/2013 | Vaught | G02B 27/017 345/633 |
| 2014/0118683 A1* | 5/2014 | Jubin | G02C 7/049 351/159.04 |
| 2014/0194708 A1* | 7/2014 | Ho | A61B 5/0004 600/318 |

* cited by examiner

DETECTING EYE MOVEMENT BASED ON A WEARABLE DETECTION APPARATUS

TECHNICAL FIELD

The present technology relates to detection apparatus and method and more particularly to detection apparatus and method that can enhance the operability with a simple configuration.

BACKGROUND ART

For example, a user interface for moving a cursor or pointer on a screen needs an operation means. As a method of detecting a user's operation for moving the cursor or the like, there are a method of detecting a movement of an operation site of a user's arm, leg, or finger that is captured by a camera based on a position of the operation site in the image and a method of detecting the movement based on a signal of a gyro sensor attached to the user's arm, leg, or finger.

In the case where the user interface operation for the cursor or pointer is performed using the user's limb, finger, or the like as described above, an external detector such as a camera and a gyro sensor is necessary.

Furthermore, in the case where the operation for moving the cursor or the pointer is performed using the line of sight of the user, it is necessary to detect an eyeball movement of the user.

Examples of the method of measuring a position or movement of the eyeball include a search coil method using the fact that a potential is generated in a coil placed in a magnetic field, the potential being proportional to an angle formed by the magnetic field and the coil. In the search coil method, a detection coil is incorporated in a contact lens. It is worn on an eyeball. A magnetic field coil that applies horizontal and vertical magnetic fields is externally placed. Induced electromotive force is generated in the detection coil incorporated in the contact lens due to the fields applied from the outside. The induced electromotive force is detected. In this manner, the eyeball movement is detected.

As another method of measuring the position or movement of the eyeball, an EOG (Electrooculography) method is also known. The EOG method uses the fact that a cornea has a positive potential of from 10 to 30 µV in comparison with a retina. Electrodes are attached around an eye. A potential difference is detected.

As other methods of measuring the position or movement of the eyeball, a limbus tracking method, a corneal reflection method, and a pupil corneal reflection method are known.

The limbus tracking method uses the feet that the reflectance of infrared light emitted to an eye differs between a sclera and iris and pupil. Light reflected by an eyeball is captured by an externally placed camera. An eyeball movement is thus detected.

Furthermore, the corneal reflection method uses the fact that a virtual image on a cornea portion that is formed of infrared LED light emitted to the eye by an infrared light LED (Light Emitting Diode) is moved in parallel along with an eyeball movement due to a rotation center difference between the cornea portion and the eyeball. The virtual image of the infrared LED light reflected by the eyeball is captured by the externally placed camera. The eyeball movement is thus detected.

The pupil corneal reflection method has the same basic principles as the corneal reflection method. However, the pupil corneal reflection method is different from the corneal reflection method in that the center of the pupil is used as a reference. That is, the pupil corneal reflection method is a method in which the center of the pupil is detected by the externally placed camera and the eyeball movement is detected based on a difference from the position of the virtual image of the infrared LED light.

By the way, as a compact image display apparatus, a contact lens type display apparatus has been proposed (e.g., see Patent Document 1). This display apparatus is used by being worn on an eyeball of the user. Therefore, irrespective of where the user is located, images can be presented to the user.

Patent Document 1: Japanese Patent No. 4752309

SUMMARY OF INVENTION

Problem to be Solved by the Invention

However, when the cursor or pointer is displayed by the above-mentioned contact lens type display apparatus and a user's operation is performed, the user interface for moving the cursor or pointer according to the above-mentioned method seeds an external detection apparatus for detecting the operation means.

Worn on the eyeball of the user, the contact lens type display apparatus is wirelessly used. The use of the external detection apparatus for operating the cursor or pointer becomes a burden because the user that uses it has to carry the extra device.

For example, in accordance with the method of detecting a movement captured by the camera, the user has to be located in an angle of view of the camera. Thus, the activity range of the user is limited. Therefore, it is difficult to take the display apparatus outside. Furthermore, as an operation distance becomes longer, an operation area in a camera screen becomes smaller. Therefore, the number of pixels for detecting the movement of the user relatively decreases. Thus, the detection accuracy is lowered.

In addition, the gyro sensor detects a relative position. Therefore, in the method of detecting the movement of the user by the gyro sensor, it is necessary to specify a reference-position for every operation.

In the search coil method, the magnetic field coil that applies the horizontal and vertical magnetic fields should be externally placed. Furthermore, the search coil method uses the electromotive force generated by the detection coil being moved relative to the magnetic field generated by the magnetic field coil. Therefore, the position of the head of the user has to be fixed with respect to the magnetic field coil.

The EOG method has a wide detection range and is capable of detecting the eyeball movement even when the user closes eyes. However, it is weak against external electromagnetic noise and the detection accuracy is low. Detection with an accuracy of less than 1 degree is impossible.

Regarding the limbus tracking method, the corneal reflection method, and the pupil corneal reflection method, all of them have less burden on a human body. However, these methods require the externally placed camera. Furthermore, it is susceptible to ambient light. Therefore, for increasing the detection, accuracy, it is necessary to prepare an environment with less ambient light.

In addition, in the method of detecting the eyeball movement by the camera capturing the user from the outside, the eyeball cannot be detected when the user closes eyes. Therefore, when the user is closing eyes, the user interface cannot be operated.

As described above, in the above-mentioned techniques, it has not been possible to enhance the operability of the contact lens type display apparatus with a simple configuration without using the external detection apparatus.

The present technology has been made in view of the above-mentioned situation and it is an object to enhance the operability with a simple configuration.

Means for Solving the Problem

A detection apparatus according to an aspect of the present technology is a detection apparatus that is wearable on an eyeball and includes a light-receiving element that receives light entering from the eyeball.

The detection apparatus may be further provided with a light-emitting element that outputs light. The light-receiving element may be provided near the light-emitting element.

The light-emitting element may be formed of a plurality of light-emitting sections, and the light-receiving element may be provided near the light-emitting section.

The light-receiving element may receive light that is output from the light-emitting section and reflected by the eyeball. A signal processing unit that detects light-receiving amounts of a plurality of light-receiving elements arranged in regions of the detection apparatus may be further provided.

The light-emitting section may be a display pixel that displays information.

The detection apparatus may be configured to cover an entire cornea portion when the detection apparatus is worn on the eyeball.

In a state in which the detection apparatus is worn on the eyeball, at least one of the light-emitting section and the light-receiving element may be provided in a region of the detection apparatus that is opposed to a region in a range in which a pupil of the eyeball is movable.

A lateral width may be set to be larger than a vertical width by which the detection apparatus covers the eyeball.

An element different from the light-emitting element and the light-receiving element may be provided near a lateral end of the detection apparatus.

The detection apparatus may have a structure for fixing the detection apparatus wife respect to a head having the eyeball.

The signal processing unit may determine a direction of the eyeball based on the light-receiving amounts of the plurality of light-receiving elements.

The signal processing unit may calculate a convergence amount of left and right eyes based on the direction of the eyeball and a direction of an eyeball that pairs with the eyeball and calculate a distance to a gazed target object based on the convergence amount.

The signal processing unit may determine a diameter of a pupil of the eyeball based on the light-receiving amounts of the plurality of light-receiving elements.

The signal processing unit may detect a living-body state based on the light-receiving amounts of the plurality of light-receiving elements.

The light-emitting section may emit light having a predetermined wavelength to the eyeball or emit light having different wavelengths to the eyeball in order, and the signal processing unit may detect the living-body state based on light-receiving amounts of the light having the predetermined wavelength or the light having the different wavelengths that is emitted to the eyeball, in the light-receiving elements.

The light-emitting section may be a display pixel that displays information. The light-emitting section may emit, after a period in which the information is displayed, the light having the predetermined wavelength or the light having the different wavelengths to the eyeball.

A detection method according to an aspect of the present technology is a detection method for a detection apparatus including a light-receiving element that receives light entering from an eyeball, and a signal processing unit that detects a light-receiving amount of the light-receiving element and being wearable on the eyeball, the method including: a light-receiving step of receiving, by the light-receiving element, light reflected by the eyeball; and a detection step of detecting, by the signal processing unit, light-receiving amounts of a plurality of light-receiving elements arranged in regions of the detection apparatus.

The detection method may further include a light-emitting step of outputting light by a light-emitting element provided in the detection apparatus. The light-receiving element may receive, in the light-receiving step, light output from the light-emitting element and reflected by the eyeball.

The detection method may further include a calculation step of determining, by the signal processing unit, a direction of the eyeball based on the light-receiving amounts of the plurality of light-receiving elements.

In the detection method, the signal processing unit may calculate, in the calculation step, a convergence amount of left and right eyes based on the direction of the eyeball and a direction of an eyeball that pairs with the eyeball and calculate a distance to a gazed target object based on the convergence amount.

In an aspect of the present technology, in the detection apparatus that includes the light-receiving element that receives light entering from the eyeball and is wearable on the eyeball, light reflected by the eyeball is received by the light-receiving element.

Effects of the Invention

According to an aspect of the present technology, it is possible to enhance the operability with a simple configuration.

MODE(S) FOR CARRYING OUT THE INVENTION

Hereinafter, embodiments to which the present technology is applied will be described with reference to the drawings.

First Embodiment

Configuration Example of Contact Lens Type Display Apparatus

The present technology relates to a contact lens type display apparatus. The contact lens type display apparatus is wirelessly used by being worn on an eyeball of the user. Therefore, when it is used for the function as the display apparatus, the user can, for example, freely walk around while wearing the display apparatus. However, performing, by an external apparatus such as a camera and a detection apparatus, an operation of selecting/moving a cursor, pointer, or the like with respect to information in a displayed screen imposes a burden or limitation on the user.

In view of this, in the present technology, light-receiving elements are provided near a display element that displays an image. Thus, a user interface for operating a cursor, pointer, or the like can be realized without needing no external apparatuses other than the display apparatus.

In the contact lens type display apparatus, reflected light on an eyeball surface of light emitted by the display element is detected by the light-receiving elements. In this case, reflected light is detected in a sclera or iris of the eyeball surface. In contrast, in a pupil portion, light passes through the eyeball and reflected light thereof is less. Thus, the portion with less reflected light is detected as the pupil. Based on the detected pupil movement, a line of sight is detected.

With this, it becomes possible to determine a direction in which the eyeball is oriented. Thus, the user interface for operating the cursor, pointer, or the like can be provided without using the external apparatus. Thus, it is possible to enhance the operability of the display apparatus with a simple configuration.

Next, a specific embodiment of the contact lens type display apparatus to which the present technology is applied will be described.

Figure 1:
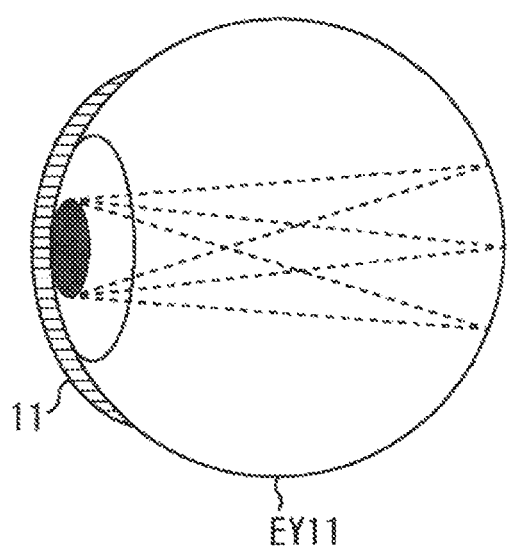
FIG. 1 A diagram showing a configuration example of the outer appearance of a display apparatus.

The contact lens type display apparatus is worn on an eyeball of the user as shown in FIG. 1.

In FIG. 1, a contact lens type display apparatus 11 is worn on a surface of an eyeball EY11 of the user. The display apparatus 11 has such a shape that it can be worn and removed on/from the eyeball EY11 of the user like a so-called contact lens.

Figure 2:
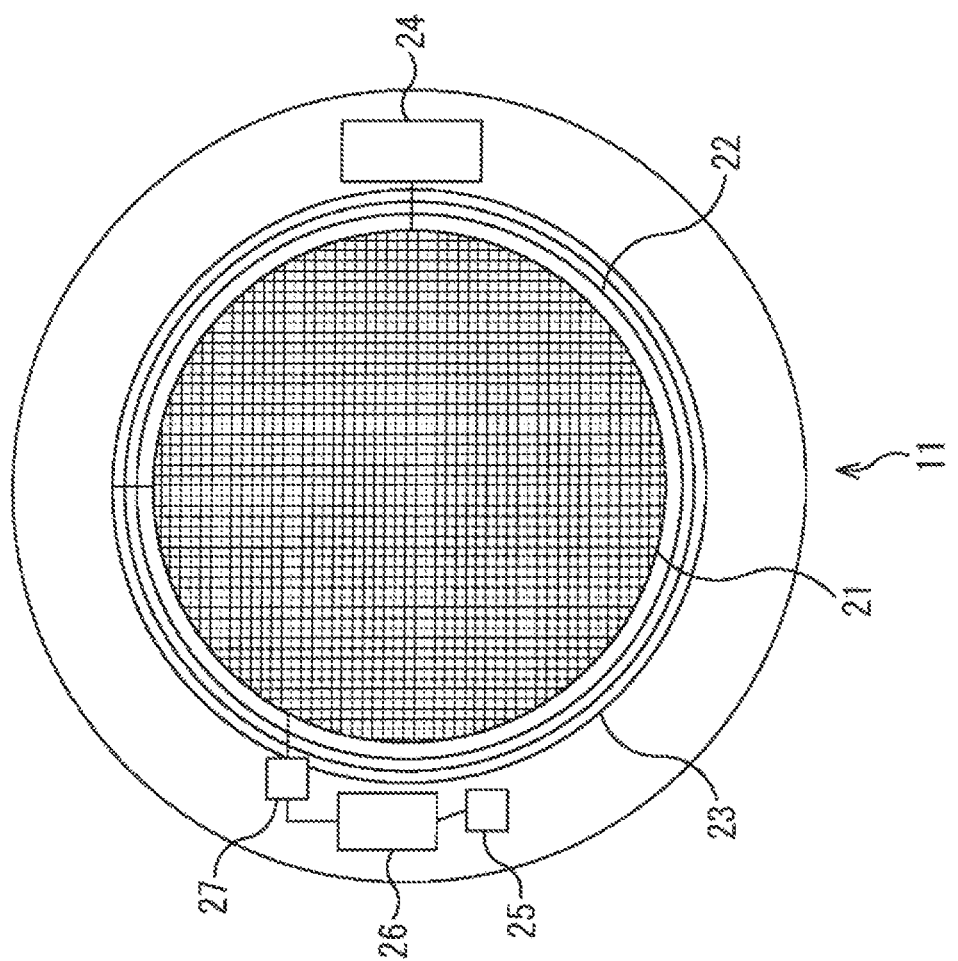
FIG. 2 A diagram showing a configuration example of the display apparatus.

Such a display apparatus 11 is, for example, configured as shown in FIG. 2.

Specifically, the display apparatus 11 is constituted of a display region 21, a feeding antenna 22, a signal antenna 23, a power generation unit 24, a sensor 25, a signal processing unit 26, and a display element drive unit 27.

Note that FIG. 2 is a diagram of the display apparatus 11 as viewed in a left-to-right direction in FIG. 1. That is, it is a diagram as the user wearing the display apparatus 11 is viewed from the front. In FIG. 2, the display apparatus 11 has a circular shape.

The display region 21 includes a display element and light-receiving elements. The display element is formed of a plurality of display pixels that display information such as an image and a character presented to the user. The light-receiving elements are arranged adjacent to the display pixels and receive light reflected by the eyeball surface of the user.

The feeding antenna 22 is provided surrounding the display region 21 and receives induced electromotive force due to a magnetic field or electric field supplied from the outside. The signal antenna 23 transmits information supplied from the signal processing unit 26, such as a result of the operation of the user interface based on the line of sight of the user, to the outside. The signal antenna 23 receives information transmitted from the outside, such as information displayed by the display pixels, and supplies it to the signal processing unit 26.

The power generation unit 24 rectifies an induced current generated in the feeding antenna 22 due to electromagnetic induction by the magnetic field or the like from the outside, to thereby obtain and store electric power and supplies the electric power to the respective sections of the display apparatus 11. Note that, in the case where the power generation unit 24 generates power by itself according to a predetermined method or includes a rechargeable battery, the display apparatus 11 does not need to be provided with the feeding antenna 22.

The sensor 25 is formed of a gyro sensor, a gravity sensor, or the like. The sensor 25 detects the posture or movement of the user wearing the display apparatus 11 and supplies a detection result thereof to the signal processing unit 26. For example, the movement of the head of the user is detected by the sensor 25.

The signal processing unit 26 controls the entire display apparatus 11. For example, based on signals supplied from the light-receiving elements of the display region 21, the signal processing unit 26 detects a difference between light-receiving amounts of light in the light-receiving elements arranged in the regions of the display apparatus 11, to thereby detect the line of sight of the user. Furthermore, based on the detection result supplied from the sensor 25, the detection result of the line of sight, the information received by the signal antenna 23, and the like, the signal processing unit 26 controls the display element drive unit 27 to display an image or the like in the display region 21.

Specifically, for example, when the display apparatus 11 is rotated relative to the eyeball of the user, the sensor 25 is capable of detecting rotation direction and rotation amount thereof. In view of this, the signal processing unit 26 controls the display element drive unit 27 to rotate the image currently displayed in the display region 21 to a direction opposite to the rotation direction of the display apparatus 11 relative to the eyeball, which is supplied from the sensor 25, by an amount corresponding to the rotation amount of the display apparatus 11. With this, even if the display apparatus 11 is rotated on the eyeball of the user, the resulting rotation of the image can be corrected and the image easy to view can be presented to the user.

The display element drive unit 27 drives the display element of the display region 21 under the control of the signal processing unit 26 to display an image or to supply the signals, which are supplied from the light-receiving elements of the display region 21, to the signal processing unit 26. Hereinafter, the signals according to the light-receiving amounts of the light-receiving elements, which are output from the light-receiving elements of the display region 21, will be referred to as light-receiving signals.

Figure 3:
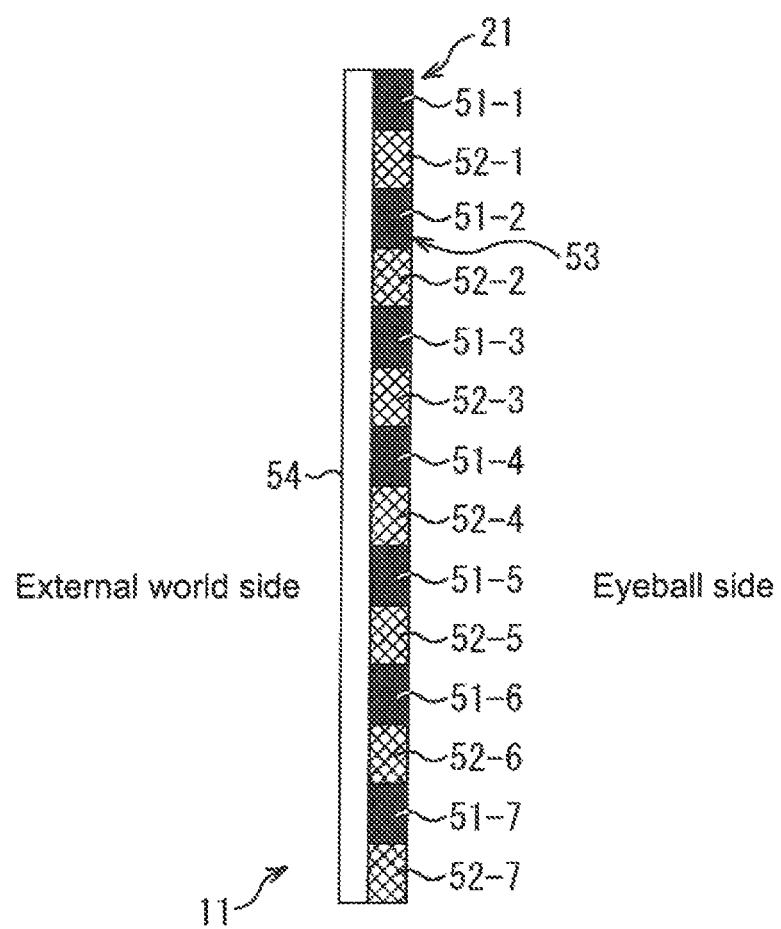
FIG. 3 A diagram showing a configuration example of a display region.

The display region 21 of the display apparatus 11 is, for example, configured as shown in FIG. 3. Note that FIG. 3 shows a part of a cross-section of the display apparatus 11 as the display apparatus 11 is viewed in a depth direction in FIG. 1.

In FIG. 3, the display region 21 of the display apparatus 11 includes display pixels 51-1 to 51-7 that display information such as an image and light-receiving elements 52-1 to 52-7 that receive reflected light entering from the eyeball surface of the user. A single display device formed of the display pixels 51-1 to 51-7 is a display element 53.

Hereinafter, in the case where the display pixels 51-1 to 51-7 do not particularly need to be distinguished from one another, they will be also simply referred to as display pixels 51. Furthermore, in the case where the light-receiving elements 52-1 to 52-7 do not particularly need to be distinguished from one another, they will be also simply referred to as light-receiving elements 52.

The display element 33 is constituted of, for example, a liquid-crystal display element or organic electroluminescence (OLED (Organic Light Emitting Diode)) display element. In the example in FIG. 3, the display pixels 51 and the light-receiving elements 52 are alternately arranged in a vertical direction on a right side of the display apparatus 11, that is, the side of the eyeball of the user in the figure. Thus, for example, in FIG. 2, the display pixels 51 and the light-receiving elements 52 are alternately arranged in vertical and lateral directions in FIG. 2 in the display region 21.

A lubricant layer 54 is provided on a left side of the display pixels 51 and the light-receiving elements 52 in the display apparatus 11 in the figure, that is, an external world side of the display apparatus 11. The lubricant layer 54 is, for example, formed of a transparent synthetic resin. Due to the lubricant layer 54, an eyelid of the user can smoothly move when the user wears the display apparatus 11 on the eye.

Referring to FIG. 3, the example in which the display pixels 51 and the light-receiving elements 52 are in close contact has been described. However, the display pixels 51 and the light-receiving elements 52 do not necessarily need to be in close contact and a clearance may be provided between the display pixels 51 and the light-receiving elements 52. Furthermore, in FIG. 3, one light-receiving element 52 is provided for one display pixel 51. However, one light-receiving element 52 may be provided for a plurality of display pixels 51.

Regarding Line-of-Sight Detections

Next, user's line-of-sight detection by the display apparatus 11 will be described.

Figure 4:
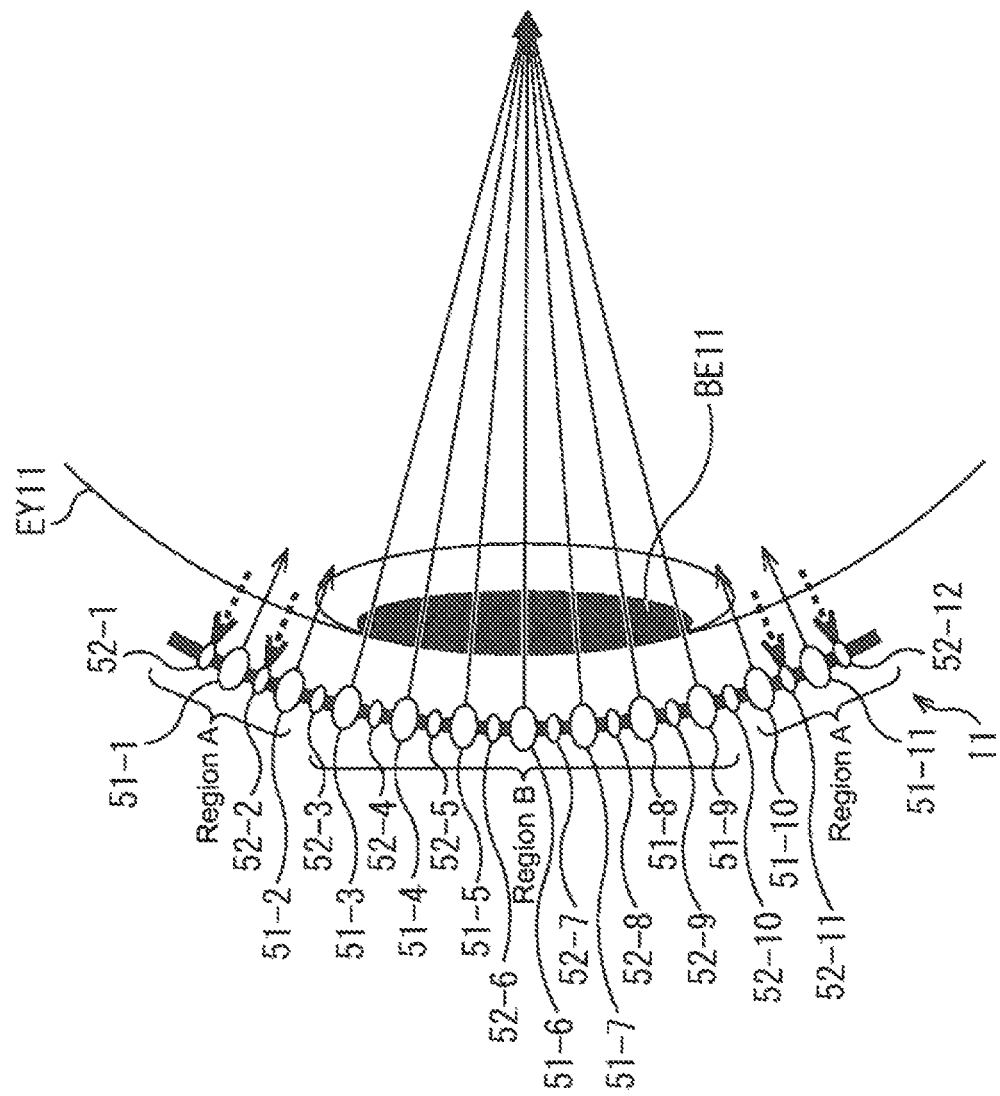
FIG. 4 A diagram for describing detection of a line of sight.

For example, as shown in FIG. 4, it is assumed that the display apparatus 11 worn on the eyeball EY11 of the user is provided with display pixels 51-1 to 51-11 and light-receiving elements 52-1 to 52-12. Furthermore, a region of the display region 21 of the display apparatus 11 that is opposed to a portion of a site of the eyeball EY11 of the user, which is different from a pupil BE11, for example, a sclera or iris will be referred to as a region A. A region of the display region 21 that is opposed to the pupil BE11 will be referred to as a region B.

When the display pixels 51 located in the regions A and B emit light, light emitted from the display pixels 51 travels to an eyeball EY11 and arrives at the eyeball EY11 as indicated by the solid-line arrow marks in the figure.

For example, some of the light output from the display pixels 51, which have entered an opaque site such as a sclera and an iris in the eyeball EY11, are absorbed and reflected by a surface of the eyeball EY11. Therefore, in the region A, some of the light output from the display pixels 51 are, as indicated by the dotted-line arrow marks, reflected by the surface of the eyeball EY11 and received (detected) by the light-receiving elements 52.

In contrast, the pupil BE11 is transparent, and hence some of the light output from the display pixels 51, which have entered the pupil BE11, are hardly reflected by the pupil BE11 but arrive at the retina in the eyeball EY11 and are absorbed by the retina. That is, as indicated by the solid-line arrow marks in the figure, in the region B, the light output from the display pixels 51 is hardly reflected by the surface of the eyeball EY11 but absorbed by the retina. Therefore, in the region B, the light output from the display pixels 51 is hardly detected by the light-receiving elements 52.

In this manner, by detecting a difference between amounts of light from the display pixels 51 that is received by the light-receiving elements 52, a direction of the eyeball EY11 indicating the direction in which the eyeball EY11 (pupil BE11) is oriented, that is, the user's line-of-sight direction can be determined. In particular, as long as the user's line-of-sight direction at each point of time can be determined, it is possible to detect an eyeball movement that is, a movement of the line of sight and also to estimate mental state or feelings of the user based on the movement of the line of sight.

Strictly speaking, little reflection occurs in all surfaces of the eyeball EY11. However, the amount of reflected light in the region B is very small in comparison with the amount of reflected light in the region A. Therefore, it is possible to sufficiently distinguish the region A from the region B.

Furthermore, in the state in which the user closes eyes, only the light, which has been output from the display pixels 51 and reflected by the eyeball EY11, enters the light-receiving elements 52. On the other hand, if the user opens eyes, when the display region 21 causes some light to pass therethrough, ambient light, which has entered the eyeball EY11 from the outside through the display region 21 and been reflected by the eyeball EY11, enters the light-receiving elements 52 together with the light output from the display pixels 51.

Also in such a case, the ambient light entering the opaque site of the eyeball EY11, such as a sclera and an iris, is reflected by the eyeball EY11 and enters the light-receiving elements 52 while most of the ambient light entering the pupil BE11 of the eyeball EY11 passes through the pupil BE11 and arrives at the retina. That is, the ambient light entering the pupil BE11 is hardly reflected and light-receiving amounts of ambient light in the light-receiving elements 52 are small. Therefore, irrespective of whether or not the user opens eyes, it is possible to sufficiently distinguish the region A from the region B.

Figure 5:
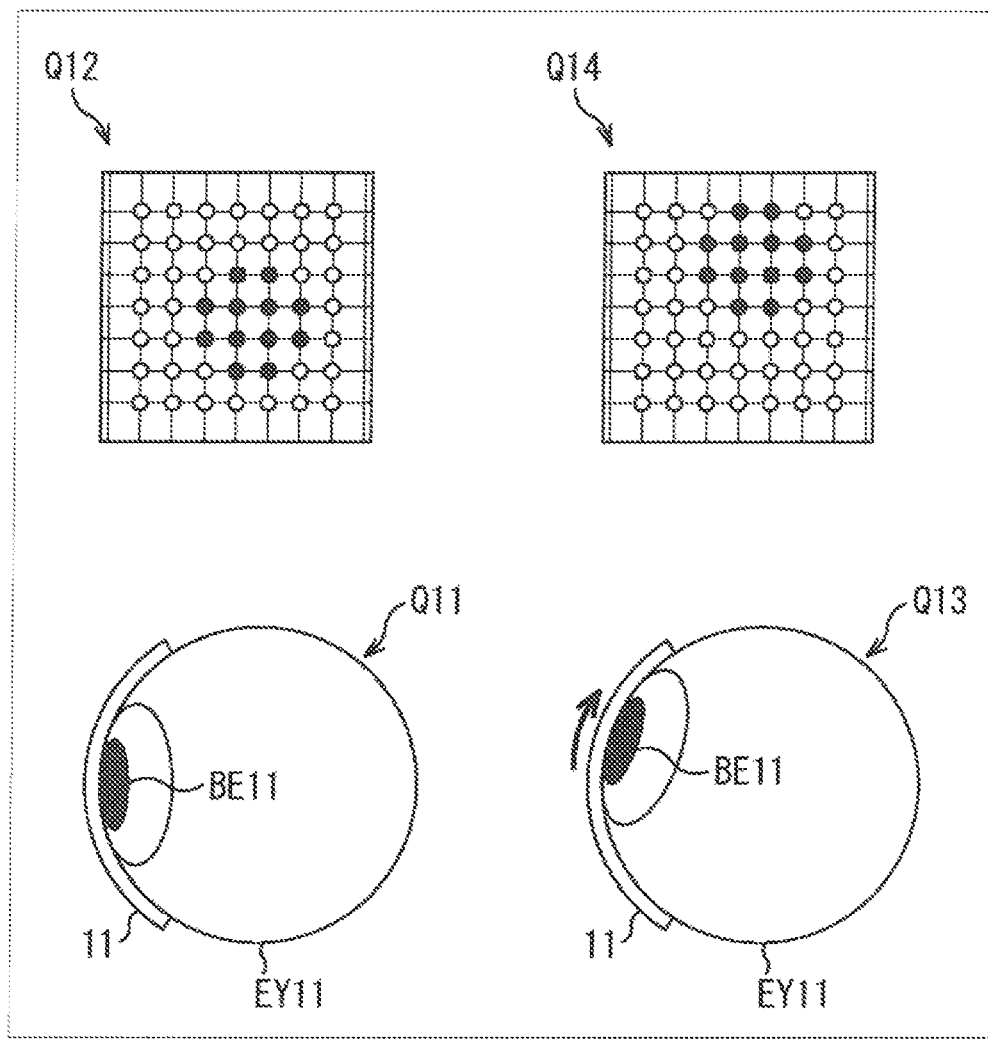
FIG. 5 A diagram for describing detection of a line of sight.

Specifically, for example, in the case where the user faces forward as indicated by an arrow mark Q11 in FIG. 5, a light-receiving signal map indicated by an arrow mark Q12 is obtained by the signal processing unit 26.

For example, the light-receiving signal map indicated by the arrow mark Q12 is image data indicating the amount of light received by each light-receiving element 52. Furthermore, the light and shade of the circles in the light-receiving signal map indicate values of the light-receiving signals output from the light-receiving elements 52 in the display region 21 that has the same positional relationship as the circles in the light-receiving signal map.

For example, a lighter circle in the light-receiving signal map indicates that the light-receiving amount of the light-receiving element 52 corresponding to the circle is larger, that is, the value of the light-receiving signal is higher. Furthermore, in this example, the light-receiving elements 52 are arranged in an array in the display region 21, and hence, also in the light-receiving signal map, the circles corresponding to the light-receiving elements 52 are arranged in the vertical and lateral directions.

In the state indicated by the arrow mark Q11, the pupil BE11 is facing to the left in the figure, and hence a user's line-of-sight direction is an approximately forward direction. Therefore, in the light-receiving signal map indicated by the arrow mark Q12 the region at approximately the center of the light-receiving signal snap that corresponds to the pupil BE11 is darker than its surrounding region. The darker region has the same circular shape as the pupil BE11. This is because reflection hardly occurs in the pupil BE11 as described above.

Furthermore, in the light-receiving signal map, the region surrounding the center region corresponding to the pupil BE11 indicates positions of portions having much reflected light, such as a sclera and an iris in the eyeball EY11.

In the display apparatus 11, intervals between the light-receiving elements 52 arranged in an array are fixed in a design phase. Therefore, based on the light-receiving signal map, a center position of the pupil BE11, that is, the line-of-sight direction can be easily calculated.

For example, the detection result of the user's line-of-sight direction is a position in the region of the display apparatus 11, which is in contact with the eyeball EY11, to which a center of the pupil BE11 is oriented, that is, a position (hereinafter, referred to as line-of-sight position) that is in contact with the center of the pupil BE11. Therefore, for example, in the example indicated by the arrow mark Q11, the position approximately at the center of the display apparatus 11 is the line-of-sight position.

In the display apparatus 11, it is also possible to calculate a diameter of the pupil BE11 based on the light-receiving signal map. For example, the region in which a value of the light-receiving signal is equal to or smaller than a predetermined value is the region of the pupil BE11 and a diameter of feat region is the diameter of the pupil BE11.

Furthermore, as indicated by an arrow mark Q13, in the case where the user looks slightly upward, a light-receiving signal map indicated by an arrow mark Q14 is obtained by the signal processing unit 26.

In the state indicated by the arrow mark Q13, the pupil BE11 is oriented in a slightly upward direction in the figure, and hence the user's line-of-sight direction is a slightly upward direction. Therefore, in the light-receiving signal map indicated by the arrow mark Q14, the region of the light-receiving signal map that corresponds to the pupil BE11 is slightly above that of the light-receiving signal map indicated by the arrow mark Q12.

As described above, in the signal processing unit 26, the line-of-sight position, that is, the direction of the eyeball EY11 can be determined by detecting the position of the pupil BE11 based on the light-receiving signal map obtained based on the light-receiving signals output from the light-receiving elements 52. In addition, in the signal processing unit 26, a position in upper, lower, left, and right directions of a target object in an image currently displayed in the display region 21 or a real space, which is gazed by the user, can be calculated based on the direction of the eyeball EY11.

Regarding Distance to Gaze Position

In the display apparatus 11, it is also possible to determine, based on the light-receiving signal map, a distance to the target object gazed by the user.

Now, referring to FIG. 6, a principle of detecting a distance to a gaze position based on directions of left and right eyeballs of the user will be described.

Figure 6:
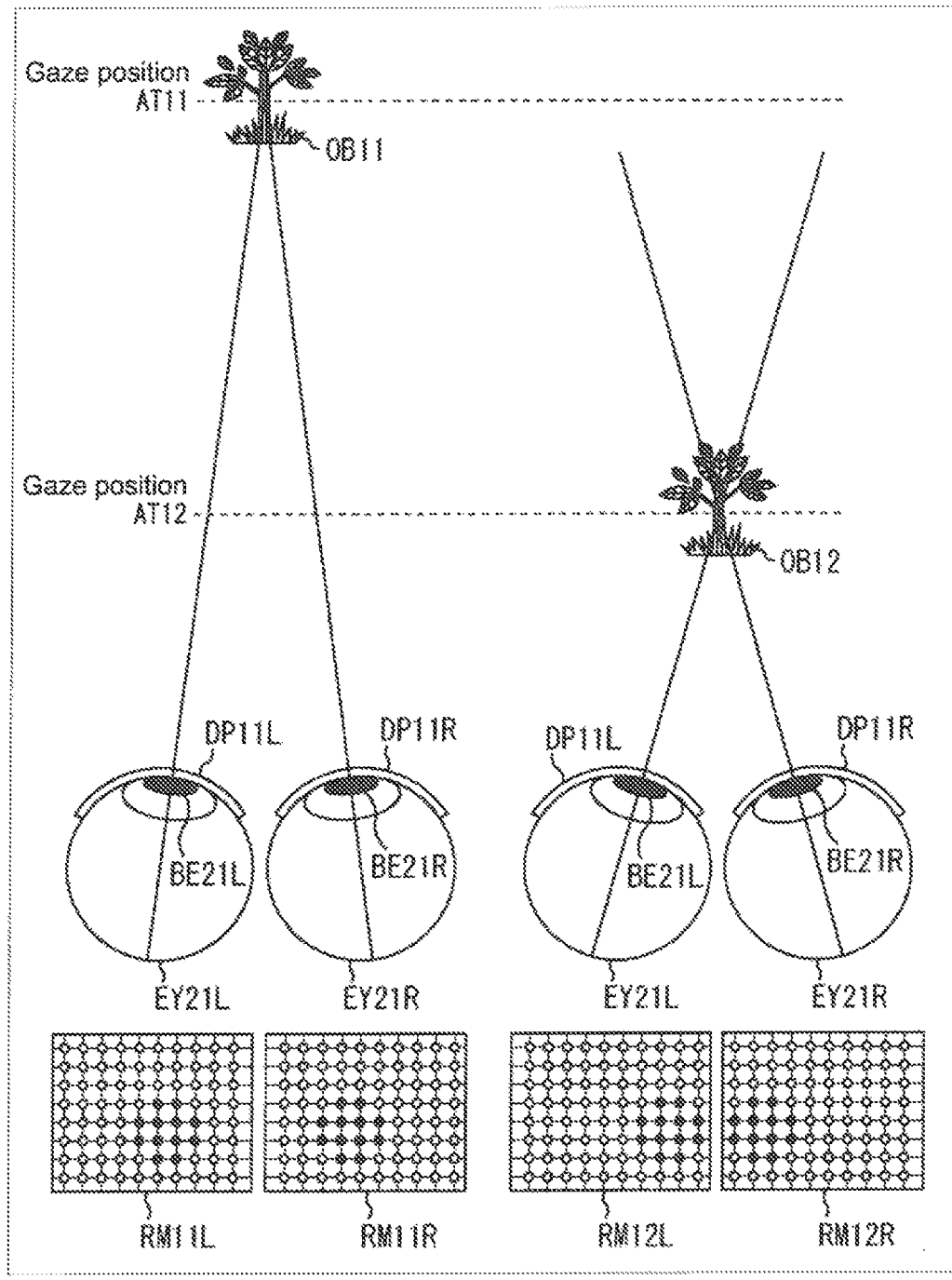
FIG. 6 A diagram for describing detection of a gaze position.

For example, as shown in FIG. 6, it is assumed that the user wears a display apparatus DP11L on a left eyeball EY21L (left eye) and a display apparatus DP11R on a right eyeball EY21R (right eye) and gazes a predetermined target object OB11 or OB12.

Here, the display apparatuses DP11L and DP11R are apparatuses each equivalent to the display apparatus 11.

In FIG. 6, the target object OB11 is located at a gaze position AT11 and the target object OB12 is located at a gaze position AT12. A distance from the user to the gaze position AT11 is longer than a distance from the user to the gaze position AT12. That is, the gaze position AT11 is further from the user than the gaze position AT12.

In general, when a person views a certain object the left and right eyes have a convergence depending on a distance to the object. That is, the left and right eyeballs rotate inward and rotation angles thereof change depending on the distance to the gazed object.

For example, in the example shown on the left side in the figure, the user gazes the target object OB11 at the gaze position AT11 approximately in front of the user. In this example, an angle formed by a straight line linking a center of the pupil BE21L of the left eyeball EY21L of the user and the target object OB11 and a straight line linking a center of the right eyeball EY21R of the pupil BE21R and the target object OB11 is a convergence angle of the user viewing the target object OB11. The convergence angle indicates a convergence amount of the left and right eyes of the user.

When the user is viewing the target object OB11 in the above-mentioned manner, a light-receiving signal map RM11L for the left eye is obtained by the display apparatus DP11L worn on the left eyeball EY21L and a light-receiving signal map RM11R for the right eye is obtained by the display apparatus DP11R worn on the right eyeball EY21R.

As can be seen from the light-receiving signal map RM11L and the light-receiving signal map RM11R, the left and right pupils BE21L and BE21R of the user are oriented slightly inward as viewed from the user.

Furthermore, for example, in the example shown on the right side in the figure, the user gazes the target object OB12 at the gaze position AT12 approximately in front of the user. In this example, an angle formed by a straight line linking a center of the pupil BE21L of the left eyeball EY21L of the user and the target object OB12 and a straight line linking a center of the pupil BE21R of the right eyeball EY21R and the target object OB12 is a convergence angle of the user viewing the target object OB12.

When the user is viewing the target object OB12 in the above-mentioned manner, a light-receiving signal map RM12L for the left eye is obtained by the display apparatus DP11L worn on the left eyeball EY21L and a light-receiving signal map RM12R for the right eye is obtained by the display apparatus DP11R worn on the right eyeball EY21R.

As can be seen from the example shown in FIG. 6, as the distance from the user to the gazed target object becomes shorter, the convergence angle of the user viewing the target object becomes larger. For example, in the example in FIG. 6, the convergence angle in viewing the target object OB12 is larger than the convergence angle in viewing the target object OB11.

Furthermore, along with this change in convergence angle, the user's pupil position (line-of-sight position) in the light-receiving signal map also changes. In the example in FIG. 6, it can be seen that, in the light-receiving signal map, the pupil position in viewing the target object OB12 is located on an inner side of the user (center side of user) in comparison with the pupil position in viewing the target object OB11.

In the display apparatus 11, the convergence angle of the left and right eyes of the user can be calculated based on the directions of the left and right eyeballs paired that is obtained based on a detection result of light at the light-receiving elements 52, that is, the pupil position in the light-receiving signal map. Based on the obtained convergence angle, the distance to the gazed object and upper, lower, left, and right positions of the gazed object can be determined.

If the distance to the gazed object can be determined in this manner, not only the position in left and right directions but also the position in the depth direction can be distinguished. Therefore, for example, when images, buttons, or the like having a parallax are displayed to the left and right eyes, an operation with a depth feeling can be realized.

In the display apparatus DP11L and the display apparatus DP11R, the convergence angle may be calculated using only the light-receiving signal map obtained based on the light-receiving signals of their own light-receiving elements 52. Alternatively, the convergence angle may be calculated using a light-receiving signal map for the left and right eyes.

In the case where the convergence angle is calculated based on the light-receiving signal map for the left and right eyes, for example, the display apparatus DP11L communicates with the display apparatus DP11R and receives the light-receiving signal map obtained by the display apparatus DP11R. Then, the display apparatus DP11L calculates a convergence angle based on the light-receiving signal map obtained by the display apparatus DP11L and the light-receiving signal map received from the display apparatus DP11R and transmits the obtained convergence angle to the display apparatus DP11R. In the calculation of the convergence angle, an eyeball direction indicating the pupil position in the light-receiving signal map for the left eye and an eyeball direction indicating the pupil position in the light-receiving signal map for the right eye is calculated.

With this, in the display apparatus DP11L and the display apparatus DP11R, the common convergence angle can be obtained. In this case, the convergence angle is calculated by the signal processing unit 26 and the convergence angle is transmitted/received by the signal antenna 23. Furthermore, the signal processing unit 26 determines the distance to the gazed object and the upper, lower, left and right positions of the gazed object using the convergence angle depending on needs. The distance to the gazed object and the like may be transmitted from the display apparatus DP11L to the display apparatus DP11R.

In addition, in the case where each of the left and right display apparatuses DP11L and DP11R calculates the convergence angle based on a single light-receiving signal map, the convergence angle is calculated based on the pupil position in the light-receiving signal map for the left or right eye. Therefore, in the case where the target object is not in front of the user, different convergence angles are obtained by the display apparatuses DP11L and DP11R. That is, left and right asymmetrical convergence angles are obtained. However, based on the left and right convergence angles, it is possible to determine the distance to the target object or the position in the left, right, upper, and lower directions of the target object.

Note that another apparatus may calculate a convergence angle based on the light-receiving signal map obtained by the display apparatus DP11L and the light-receiving signal map obtained by the display apparatus DP11R.

Figure 7:
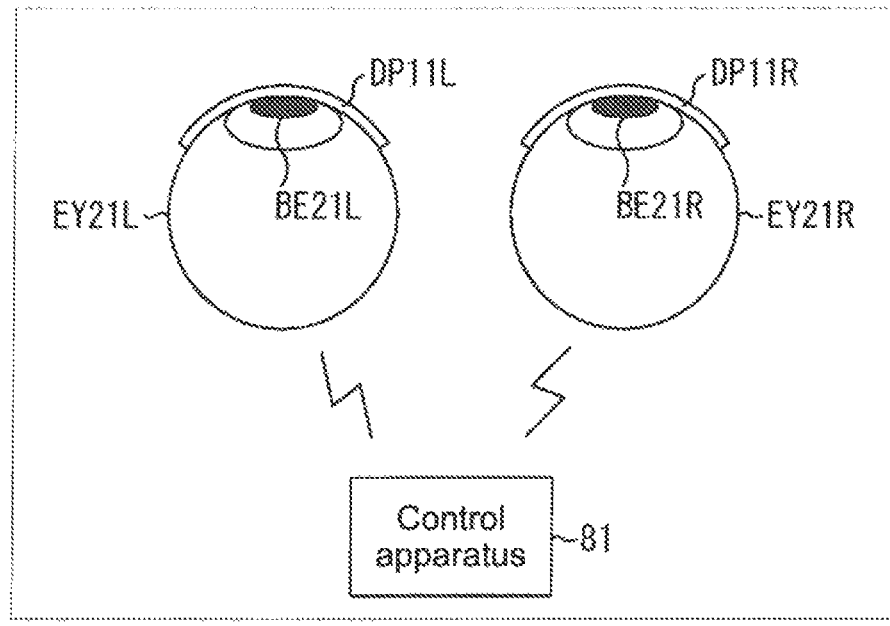
FIG. 7 A diagram for describing processing by a control apparatus.

In such a case, for example, as shown in FIG. 7, a control apparatus 81 communicates with the display apparatuses DP11L and DP11R and receives the light-receiving signal maps.

Then, the control apparatus 81 calculates a convergence angle based on the light-receiving signal map received from the display apparatus DP11L and the light-receiving signal map received from the display apparatus DP11R and transmits the obtained convergence angle to the display apparatuses DP11L and DP11R.

Note that the control apparatus 81 may be configured to calculate the distance to the target object or the position or the like of the target object based on the convergence angle and transmit it to the display apparatuses DP11L and DP11R.

As described above, according to the display apparatus 11, it is possible to directly receive reflected light from the eyeball and detect the eyeball movement, that is, the eyeball direction (line-of-sight position) at each point of time. In particular, due to the provision of the plurality of light-receiving elements 52 in the display region 21, it becomes possible to accurately detect little movements of the eyeball.

Regarding Detection of Microsaccades

By the way, it is known that eyeball movements include little movements called saccades. In particular, the largest movements of involuntary eyeball movements that occur during visual fixation are called microsaccades.

Instead of being random, these little ocular shifts may point to where mind of a person is secretly focusing even if his/her gaze is directed elsewhere revealing hidden thoughts and desires.

Therefore, if the display apparatus 11 detects microsaccades, it becomes possible to determine not only a target object gazed by the user but also a target object in which the user is potentially interested.

Specifically, for example, the signal processing unit 26 detects, based on the light-receiving signal map at each point of time, an eyeball direction, that is, a line-of-sight position at each point of time. Then, if the same line-of-sight position is detected at most points of time in a predetermined period, this line-of-sight position is a position gazed by the user, that is, a position of the target object which the user focuses on.

Furthermore, the signal processing unit 26 detects one of the line-of-sight positions different from the position gazed by the user, which is obtained at a point of time at which the movement of the eyeball direction is largest in the above-mentioned predetermined period, as a position of the target object in which the user is potentially interested. That is, the largest eyeball movement is detected as a microsaccade.

Regarding Detection of Living-Body State

The display apparatus 11 is also capable of detecting a living-body state.

For example, the display apparatus 11 is capable of detecting pulsations of the heart of the user as the living-body state. Hereinafter, a principle of detecting the pulsations will be described.

In the display apparatus 11, the display pixels 51 output light having a predetermined wavelength and light reflected by the eyeball surface is received by the light-receiving elements 52. Then, the signal processing unit 26 detects pulsations of the heart of the user wearing the display apparatus 11 based on values of the light-receiving signals supplied from the light-receiving elements 52 via the display element drive unit 27.

Figure 8:
FIG. 8 A diagram showing pulsations of a heart.

For example, the pulsations of the heart are periodically generated as shown in FIG. 8. A pulsation time is short with respect to a cycle and a blood flow is generated at a pulsation timing. Note that, in FIG. 8, the horizontal axis indicates a time and the vertical axis indicates a value of a light-receiving signal, that is, a blood flow rate.

As can be seen from FIG. 8, portions at which the blood flow rate shapely changes are pulsation portions and the pulsations are periodically generated.

At a timing at which the blood flow rate is increased due to a pulsation, the blood flowing through capillary vessels increases. Thus, it is possible to defect a pulsation based on the presence/absence of a blood flow. The capillary vessels extend through the eyeball and have blood flows depending on pulsations of the heart.

Oxyhemoglobin and deoxyhemoglobin that are components in blood have different spectral characteristics of light absorption. The deoxyhemoglobin has a high absorption coefficient with a wavelength shorter than 805 nm. The oxyhemoglobin has a high absorption coefficient with a wavelength longer than 805 nm.

In view of this, the signal processing unit 26 controls the display element drive unit 27 to output, from the display pixels 51, light having a predetermined wavelength shorter than the wavelength of 805 nm and light having a predetermined wavelength longer than the wavelength of 805 nm in order (alternately). Furthermore, the signal processing unit 26 causes the light-receiving elements 52 to receive light output from the display pixels 51 and reflected by the eyeball surface. Here, the light having a wavelength shorter than 805 nm may be visible light.

Then, the signal processing unit 26 determines a difference between a value of a light-receiving signal obtained when the short-wavelength light is output and a value of a light-receiving signal obtained when the long-wavelength light is output, to thereby determine which component of oxyhemoglobin and deoxyhemoglobin is more contained in the blood. In addition, the signal processing unit 26 detects a blood flow (change in blood flow rate) based on a determination result obtained based or the difference between the light-receiving signals and changes in the values of the light-receiving signals at respective points of time in a predetermined period, that is, variations over time in the intensity of reflected light received by the light-receiving elements 52. Then, the signal processing unit 26 determines a pulsation based on the detection result of the blood flow.

Hemoglobin in the blood has a strong absorption spectrum with respect to light of a certain wavelength band. Reflected light in blood (blood vessel) when the light of the certain wavelength band is emitted thereto varies depending on an amount of hemoglobin that varies depending on variations in the capacity of the blood vessel. Therefore, the blood flow rate can be detected based on the intensity of reflected light emitted to the surface of the eyeball (capillary vessels).

Note that the blood flow rate itself may be detected as the living-body state by the signal processing unit 26.

Furthermore, the display apparatus 11 is also capable of detecting a congestion degree of the eyeball.

The congestion of the eyeball is a phenomenon in which blood vessels of the sclera surface are dilated and stand out due to some influences and the eye looks red and congested. The blood flow rate in the case of congestion is higher than normal.

For example, if the eye surface has conjunctivitis due to infection of bacteria or virus, the eye is congested. Otherwise, blood vessels are dilated for feeding more blood to the blood vessels for supplementing oxygen and nutrient if the eyes are abused by using a personal computer, playing a television game, or reading a book for a long time, if there are influences of contact lenses, or if the eyes are not sufficiently rested. It also results in the eye congestion.

The signal processing unit 26 of the display apparatus 11 performs the same processing as the case described above in the detection of the pulsations of the heart to detect the blood flow rate in the eyeball of the user and compare the normal blood flow rate with the detected blood flow rate. The eye congestion degree is thus determined. By comparing the blood flow rates with each other, for example, determining the difference between the blood flow rates, an increase of the blood flow rate in comparison with the normal blood flow rate can be detected. Note that the normal blood flow rate may be a value set in advance or may be a value determined based on blood flow rates in the past.

By the display apparatus 11 detecting the congestion degree of the eye of the user, it becomes possible to judge whether or not the eyeball has an abnormality due to fatigue or disease.

As described above, the display apparatus 11 detects the living-body state (human body state) such as a heart rate and an eye congestion degree, and hence a detection result thereof can be used for various application programs and the like.

For example, an increase of the heart rate when the user is surprised or excited can be detected by the display apparatus 11. In addition, the display apparatus 11 is capable of determining an object that causes the surprise or excitement based on the line of sight (eyeball movement) of the user and a detection result of microsaccades.

Regarding Display Region

Figure 9:
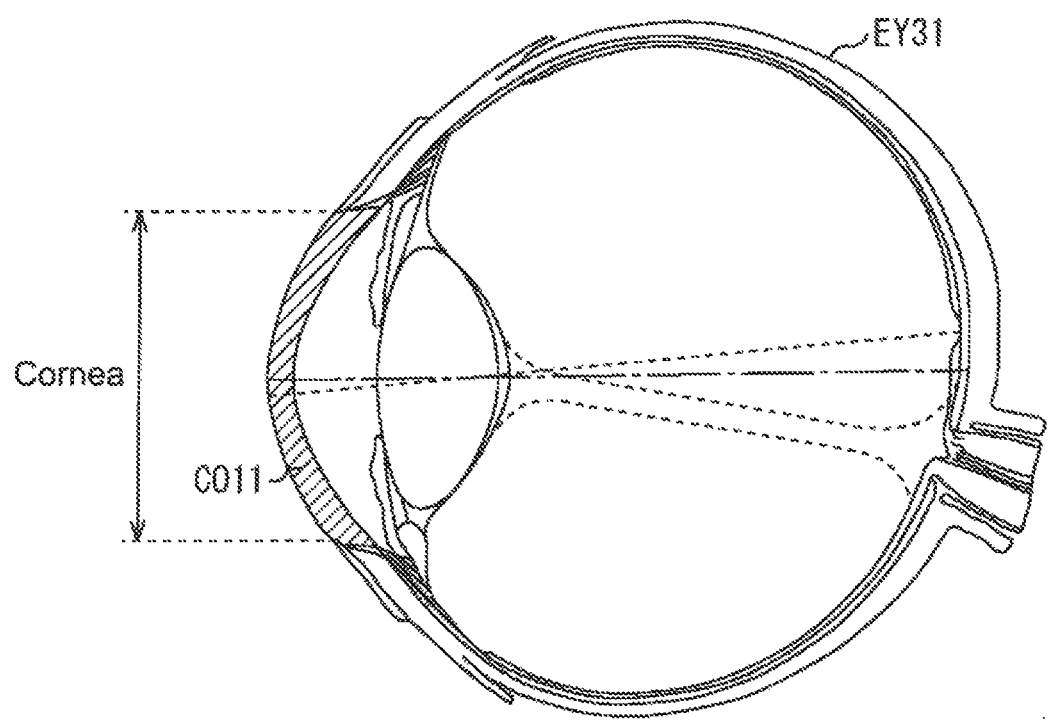
FIG. 9 A diagram showing an eyeball.

By the way, the display apparatus 11 has a structure such that it covers an area larger than the cornea portion of the eyeball shown in FIG. 9. In FIG. 9, a hashed portion of an eyeball EY31 expresses a cornea portion CO11.

The display apparatus 11 has size and shape such that it covers the entire cornea portion CO11 when the display apparatus 11 is worn on the eyeball EY31.

Figure 10:
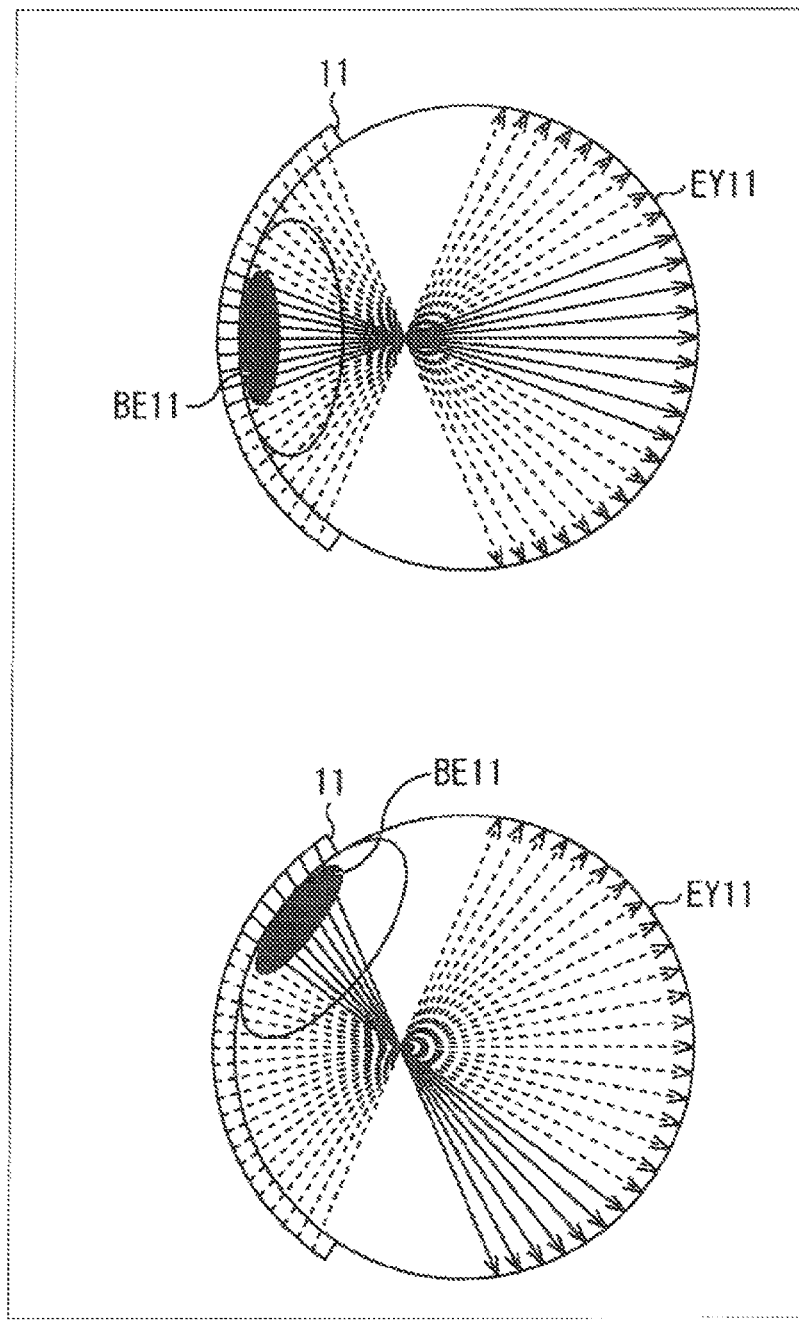
FIG. 10 A diagram for describing a movement range of a pupil.

For example, as shown on the upper side in FIG. 10, in the state in which the user faces forward, the pupil BE11 of the eyeball EY11 is also oriented forward. Note that, in FIG. 10, portions corresponding to those in FIG. 4 will be denoted by the same reference symbols and descriptions thereof will be appropriately omitted.

In the example shown, on the upper side in FIG. 10, the pupil BE11 is oriented forward and light output from the display pixels 51 of the display apparatus 11 travels to the eyeball EY11.

Note that solid-line arrow marks in the figure indicate some of the light output from the display pixels 51, which pass through the pupil BE11 and arrive at the retina. Dotted-line arrow marks in the figure indicate light beams when some of the light output from the display pixels 51, which do not pass through the pupil BE11 but are absorbed or reflected by the eyeball EY11, arrive at the retina without being absorbed and reflected by the surface of the eyeball EY11, for example.

As can be seen from the example on the upper side in the figure, light output from the display pixels 51 in a region of the display apparatus 11 that is opposed to the pupil BE11 arrives at the retina and light output from the display pixels 51 in a region opposed to a portion different from the pupil BE11 does not arrive at the retina.

Furthermore, on the lower side in the figure, shown is the state of the eyeball EY11 when the user looks upward. In this example, in comparison with the example on the upper side in the figure, the pupil BE11 moves toward an end (circumference) of the display apparatus 11 and light output fem the display pixels 51 near an upper end of the display apparatus 11 passes through the pupil BE11 and arrives at the retina. Furthermore, light output from the display pixels 51 near the center of the display apparatus 11 does not pass through the pupil BE11 and is reflected or absorbed on/in the surface of the eyeball EY11.

In the display apparatus 11, the display pixels 51 and the light-receiving elements 52 are provided in an entire region of the entire region of the display apparatus 11, which is opposed to a region in a range in which the pupil BE11 is movable along with a movement of the eyeball EY11 as shown in FIG. 10, more specifically, a range in which the pupil BE11 moves in daily life. In other words, irrespective of which direction the eyeball EY11 is oriented, the display pixels 51 and the light-receiving elements 52 are arranged near the region of the display apparatus 11 that is opposed to the pupil BE11.

With this, even if the eyeball EY11 is moved in the user interface operation, it becomes possible to prevent reduction of information due to lack of information displayed by the display pixels 51. That is, irrespective of which direction the line of sight of the user is oriented, it is possible to present the information the user by the display pixels 51 and detect a user's line-of-sight position by the light-receiving elements 52. In this case, light for displaying an image is emitted from a full field of the user and the image is displayed in an entire visual field of the user.

Note that, in a region of a wider range (movement range of pupil) in comparison with the center of the display apparatus 11, at least the display pixels 51 or the light-receiving elements 52 only need to be provided. It is not necessarily necessary to provide the display pixels 51 and the light-receiving elements 52 in an entire range in which the eyeball moves.

Description of Calibration Processing

Next, operations of the display apparatus 11 will be described.

For example, for the user interlace operation using an eyeball movement due to a movement of the line of sight of the user, the display apparatus 11 can perform calibration processing, to thereby accurately correct a positional relationship between the user's line-of-sight position and the position of information displayed in the display region 21.

Figure 11:
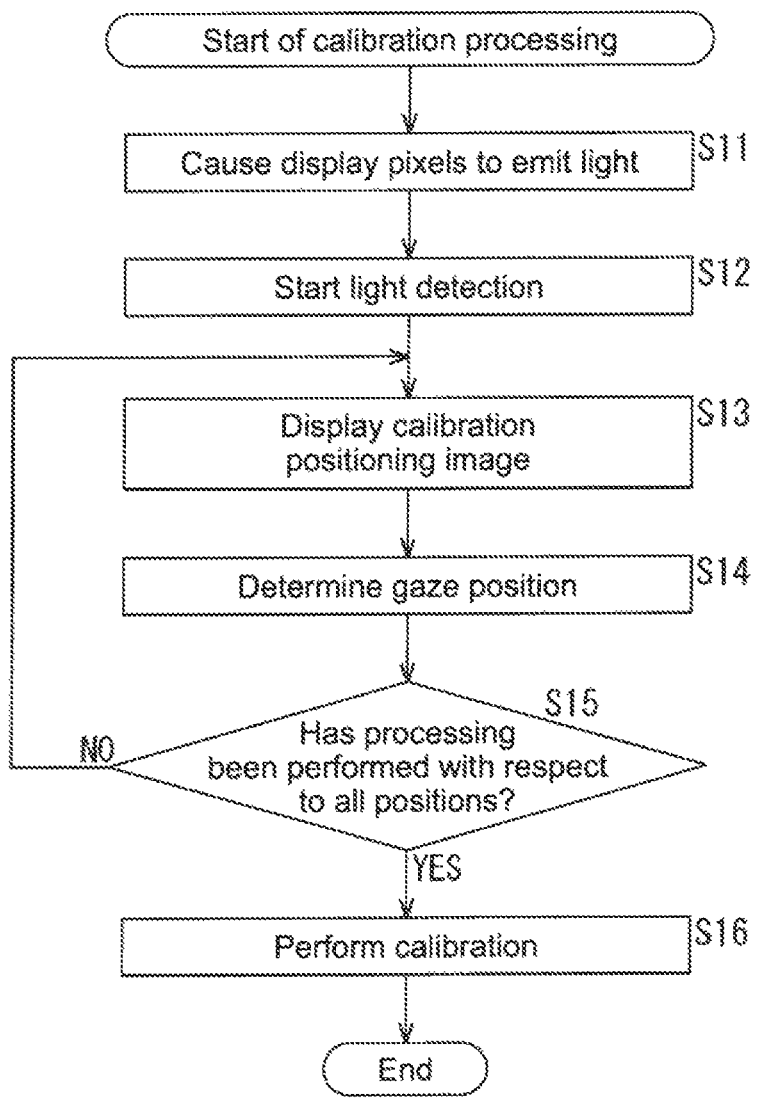
FIG. 11 A flowchart for describing calibration processing.

Hereinafter, referring to a flowchart in FIG. 11, calibration processing by the display apparatus 11 will be described. The calibration processing is started, for example, when the user wears the contact lens type display apparatus 11 on the eyeball.

In Step S11, the signal processing unit 26 controls the display element drive unit 27 to cause the display pixels 51 to emit light. The display pixels 51 emit light under the control of the display element drive unit 27 and output light for displaying a predetermined image.

In Step S12, the light-receiving elements 52 start detection of light entering from the eyeball. That is, the light-receiving elements 52 receive light that has entered the eyeball from the outside of the display apparatus 11 or the display pixels 51 and been reflected by the eyeball surface. Then, the light-receiving elements 52 perform photoelectric conversion and supplies light-receiving signals according to light-receiving amounts to the signal processing unit 26 via the display element drive unit 27.

In Step S13, the signal processing unit 26 controls the display element drive unit 27 to cause the display pixels 51 to display a calibration positioning image. The display pixels 51 emit light under the control of the display element drive unit 27, to thereby display the calibration positioning image.

For example, an image or the like of a mark for calibration is used as the calibration positioning image. Calibration positioning images are displayed at five positions of the center and upper, lower, left, and right positions of the display region 21 in order.

In Step S13, the signal processing unit 26 selects a position in which the calibration positioning image is not yet displayed from among the center and the upper, lower, left, and right positions and displays the calibration positioning image at the selected position.

Furthermore, together with the calibration positioning images, a message for prompting the user to view the calibration positioning images and perform an operation for determining the position may be displayed in the display region 21 depending on needs.

When the calibration positioning images are displayed, light for displaying the calibration positioning images is output from the display pixels 51 and some of the light are reflected by the eyeball surface and received by the light-receiving elements 52. Then, the light-receiving elements 52 supply the light-receiving signals according to the amounts of light received to the signal processing unit 26 via the display element drive unit 27.

Furthermore, the user looks at the calibration positioning image and performs a position determination operation, for example, gazing the calibration positioning image for a predetermined time or longer or blinking.

In Step S14, the signal processing unit 26 determines a user's line-of-sight position based on the light-receiving signals supplied from the light-receiving elements 52.

For example, if the motion of gazing the same position for a predetermined time or longer is set as the position determination operation performed by the user, the signal processing unit 26 generates a light-receiving signal map based on light-receiving signals and determines a user's line-of-sight position at each point of time based on the obtained light-receiving signal map.

Then, the signal processing unit 26 sets the same one of the determined line-of-sight positions at the points of time, which is successively detected for a predetermined time or longer, as a line-of-sight position with respect to the calibration positioning image. That is, the set line-of-sight position is considered as a line-of-sight position when the user views the calibration positioning image.

Furthermore, for example, if the blinking motion is set as the position determination operation performed by the user, the signal processing unit 26 generates a light-receiving signal map based on light-receiving signals, detects user's blinking based on the light-receiving signal map at each point of time, and determines a user's line-of-sight position at each point of time.

Then, the signal processing unit 26 sets the users line-of-sight position at the point of time when the blinking is detected, as the line-of-sight position with respect to the calibration positioning image.

The blinking detection is performed based on, for example, light intensity detected by the light-receiving elements 52, that is, a value (value of light-receiving signal) at each position of the light-receiving signal map.

When the user opens the eyelid, light received by the light-receiving elements 52 includes ambient light in addition to light from the display pixels 51. Therefore, between the state in which the user opens the eyelid and the state in which the user closes the eyelid, the light intensity received by the light-receiving elements 52 differ. Therefore, the user's blinking can be detected based on a change in a light amount level detected by the light-receiving elements 52, that is, the value of the light-receiving signal. Note that, by considering a temporal change in addition to the change in the light amount level, it is possible to further enhance the detection accuracy of the blinking.

In Step S15, the signal processing unit 26 determines whether or not the processing has been performed with respect to all the positions. For example, if calibration positioning images are displayed at the center and the upper, lower, left, and right positions of the display apparatus 11 and the line-of-sight position is determined for each of the positions, it is determined that the processing has been performed with respect to all the positions.

In Step S15, if the processing has not yet been performed with respect to all the positions, the processing returns to Step S13 and the above-mentioned processing is repeated. That is, the calibration positioning image is displayed at a next position and a line-of-sight position is determined.

In contrast if it is determined in Step S15 that the processing has been performed with respect to all the positions, the signal processing unit 26 in Step S16 performs calibration and the calibration processing ends.

For example, the signal processing unit 26 determines, with respect to each position, a deviation amount between a display position of the calibration positioning image and a line-of-sight position when the calibration positioning image is displayed at that position and performs calibration. That is, a correction value for making the display position of the image in the display region 21 coincide with the line-of-sight position when the user actually gazes that image is determined.

In the above-mentioned manner, the display apparatus 11 displays the calibration positioning image and performs calibration based on the display position and the user's line-of-sight position. By performing a calibration in this manner, it is possible to accurately correct the deviation between the display position and the line-of-sight position and to enhance the operability of the display apparatus 11.

Description of Line-of-Sight Detection Processing

When the calibration processing is performed, the user can activate an arbitrary application program and execute desired processing.

For example, during execution of the application program, the user can move the line of sight and perform various operations. In such a case, the display apparatus 11 performs the line-of-sight detection processing to detect the user's line-of-sight position and performs processing depending on a detection result thereof.

Figure 12:
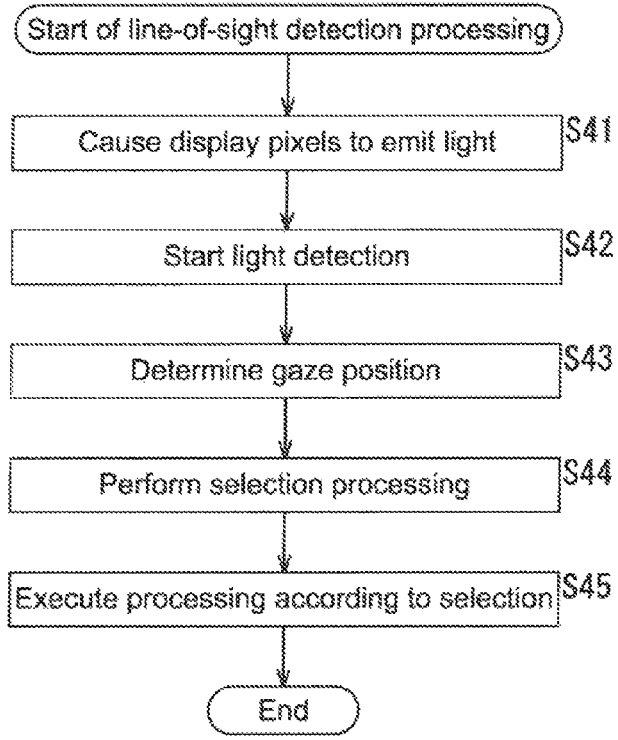
FIG. 12 A flowchart for describing line-of-sight detection processing.

Hereinafter, referring to a flowchart in FIG. 12, the line-of-sight detection processing by the display apparatus 11 will be described.

In Step S41, the signal processing unit 26 controls the display element drive unit 27 and causes the display pixels 51 to emit light. The display pixels 51 emit light according to the control of the display element drive unit 27 and outputs light for displaying a predetermined image. With this, for example, a button or pointer for information selection is displayed in the display region 21 depending on needs.

In Step S42, the light-receiving element 52 start detection of light entering from the eyeball. That is, the light-receiving elements 52 receive light that has entered the eyeball from the outside of the display apparatus 11 or the display pixels 51 and been reflected by the eyeball surface, performs photoelectric conversion, and supply light-receiving signals according to light-receiving amounts to the signal processing unit 26 via the display element drive unit 27.

In Step S43, the signal processing unit 26 determines a user's line-of-sight position based on the light-receiving signals supplied from the light-receiving elements 52. That is, the signal processing unit 26 generates a light-receiving signal map based on the light-receiving signals and detects a pupil center (eyeball direction) of the user based on the obtained light-receiving signal map.

In Step S44, the signal processing unit 26 performs the selection processing based on the line-of-sight position.

For example, if the pointer or cursor is displayed in the display region 21, according to a movement of the line-of-sight position, the signal processing unit 26 controls the display element drive unit 27 to drive the display pixels 51 to move the pointer or cursor displayed in the display region 21 (display pixels 51). For example, control is performed such that the pointer or the like is displayed at the line-of-sight position.

Furthermore, if the pointer or cursor, that is, the user's line-of-sight position is located in the region of the selection target such as a button or icon displayed in the display region 21, the signal processing unit 26 determines that the selection target thereof is selected. Note that if the user's line-of-sight position is at the position of the selection target for a predetermined time or longer, it may be determined that the selection target is selected.

In addition, for example, even if an indication means such as a pointer is not displayed in the display region 21, when the line-of-sight position is located in the region of the selection target such as a button, it may be determined that the selection target is selected.

In addition to this, if the user blinks a predetermined number of times, for example, one time or a plurality of times in the state in which the user's line-of-sight position is located at the selection target such as a button or if the user closes the eyelid for a predetermined time or longer in the state in which the line-of-sight position is located at the selection target suck as a button, the selection target may be selected. In this case, the signal processing unit 26 detects, based, on the light-receiving signal map, blinking and a line-of-sight position, or a time for which the user is closing eyes, such that selection processing is performed on the selection target.

Furthermore, if images having a parallax are presented to the paired left and right eyes of the user, the selection processing is performed using the distance from the user to the gaze position. In this case, the signal antenna 23 receives an eyeball direction or light-receiving signal map from a display apparatus 11 worn on the other eyeball that pairs with the one eyeball and supplies it to the signal processing unit 26. Then, the signal processing unit 26 calculates the convergence angle based on the eyeball direction (line-of-sight position.) obtained in Step S43 and the received eyeball direction or light-receiving signal map and calculates the distance to the gaze position based on the obtained convergence angle.

In addition, the signal processing unit 26 may control the display pixels 51 via the display element drive unit 27 and display the selected selection target such as a button in color and shape different from color and shape of other selection targets that are not selected, that is, in a different display manner. With this, the user can easily know which selection target is selected.

Note that the selection target is not limited to the button or the like and any target, for example, image and character information can be used as long as it can be a selection target.

In Step S45, the signal processing unit 26 executes processing according to selection by the selection processing in Step S44 and the line-of-sight detection processing ends.

For example, the signal processing unit 26 executes the software or calculation associated with the selected selection target or controls the display pixels 51 to display the image and character information set as the selection target in an enlarged manner. Furthermore, according to selection in the selection processing, the diameter or the like of the pupil may be determined based on the light-receiving signal map as the information used in an application program, for example.

Note that, in Step S45, the processing according to the detection result of the above-mentioned living-body state or the detection result of microsaccades and selection by the selection processing may be executed.

In the above-mentioned manner, the display apparatus 11 receives light from the display pixels 51 or the like by the light-receiving elements 52, detects the line-of-sight position based on the obtained light-receiving signals, performs selection processing based on the line-of-sight position, and executes processing according to a selection result thereof.

In this manner, by detecting the line-of-sight position based on the light-receiving signals obtained by the light-receiving elements 52, it is possible to easily determine the users operation without needing the external apparatus other than the display apparatus 11. In other words, it is possible to enhance the operability of the display apparatus 11 with a simple configuration.

Furthermore, in the display apparatus 11, even in the state in which the user closes eyes, it is possible to detect the eyeball direction, that is, the line-of-sight position at high accuracy. Here, the detection accuracy of the line-of-sight position can be made higher as the distance (pitch) between the light-receiving elements 52 proximate to each other in the display region 21 is made shorter.

Description of Living-Body State Detection Processing

In addition, in the display apparatus 11, the living-body state can be detected.

Figure 13:
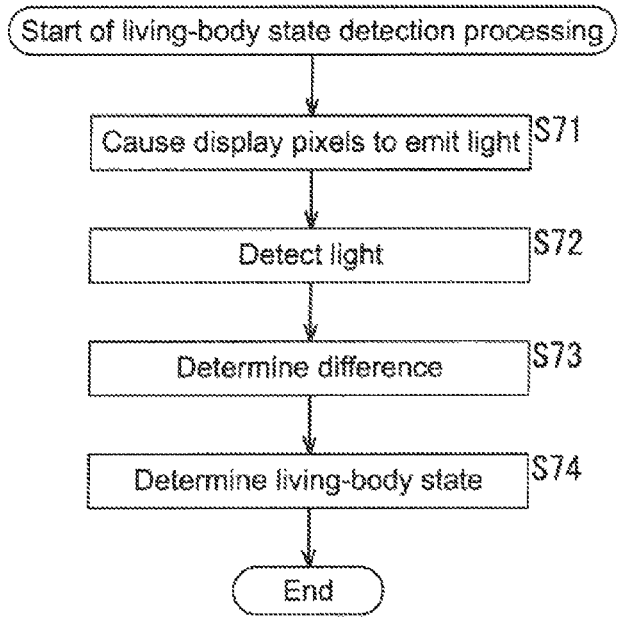
FIG. 13 A flowchart for describing living-body state detection processing.

Hereinafter, referring to a flowchart in FIG. 13, the living-body state detection processing by the display apparatus 11 will be described.

Note that the living-body state detection processing is performed alternating with the line-of-sight detection processing described with reference to FIG. 12, for example. That is, the line-of-sight detection processing is performed for a period for which information of an image or the like is displayed in the display region 21. After that period, the living-body state detection processing is performed and the living-body state is detected. Still after that, the image or the like is displayed again in the display region 21 and the line-of-sight detection processing is performed. After that, the line-of-sight detection processing and the living-body state detection processing are alternately performed.

In Step S71, the signal processing unit 26 controls the display element drive unit 27 to cause the display pixels 51 to emit light. The display pixels 51 emit light under the control of the display element drive unit 27 and outputs light having a predetermined wavelength band set in advance.

In Step S72, the light-receiving elements 52 detect light entering from the eyeball. That is, the light-receiving elements 52 receive light that has entered the eyeball from the outside of the display apparatus 11 or the display pixels 51 and been reflected by the eyeball surface, perform photoelectric conversion, and supply light-receiving signals according to light-receiving amounts to the signal processing unit 26 via the display element drive unit 27.

Note that the processes in Steps S71 and S72 are alternately performed a predetermined number of times for each wavelength of the light output from the display pixels 51.

For example, if the pulsations of the heart, the blood flow rate, the eye congestion degree, and the like are detected as the living-body state, reception and output of light having a predetermined wavelength shorter than 805 nm as described above and reception and output of light having a predetermined wavelength shorter than 805 nm are alternately performed.

In the case of detecting the living-body state, in the state in which the line-of-sight detection processing is not performed, light from the display pixels 51 is detected in the light-receiving elements 52. Therefore, during detection of the living-body state, the light-receiving elements 52 are not influenced by light for displaying an image, which is output from the display pixels 51 when the line-of-sight detection processing is performed, and hence the living-body state can be detected more accurately.

The example is which the light having two particular wavelengths is output from the display pixels 51 has been described. Alternatively, while changing the wavelength of the light output from the display pixels 51 over time, light beams having each of three or more wavelengths in a particular wavelength band may be emitted to the eyeball in order.

In Step S73, the signal processing unit 26 determines a difference between light-receiving signals at the points of time. For example, a difference between a light-receiving signal obtained when outputting the short-wavelength light and a light-receiving signal obtained when outputting the long-wavelength light, it is possible to determine which component of oxyhemoglobin and deoxyhemoglobin is contained in the blood.

In Step 74, the signal processing unit 26 determines a living-body state based on the light-receiving signal at each point of time obtained in Step S72.

For example, if pulsations of the heart are detected as the living-body state, the signal processing unit 26 detects a blood flow (change in blood flow rate) based on the difference obtained in Step S73 and variations in the light-receiving signals at the points of time in the predetermined period obtained in Step S72 and determines a pulsation based on the detection result of the blood flow.

Furthermore, for example, if the congestion degree of the eyeball is detected as the living-body state, the signal processing unit 26 may detect the blood flow rate in the eyeball of the user based on variations in the light-receiving signals at the points of time in the predetermined period and compares the normal blood flow rate retained in advance with the detected blood flow rate, to thereby determine the eye congestion degree. Note that the blood flow rate itself may be detected as the living-body state.

When determining the living-body state such as pulsations of the heart and an eye congestion degree, the signal processing unit 26 outputs the information indicating the obtained living-body state to the application program using the living-body state and terminates the living-body state detection processing.

For example, the information indicating the living-body state is recorded in the signal processing unit 26 or transmitted from the signal processing unit 26 to the outside via the signal antenna 23 to be used in the application program. Furthermore, the information indicating the living-body state may be used for the selection processing or the like of the selection target in the signal processing unit 26.

In the above-mentioned manner, the display apparatus 11 outputs light having a particular wavelength from the display pixels 51. The light is received by the light-receiving elements 52. The living-body state is detected based on the resulting light-receiving signals.

By the light-receiving elements 52 receiving the light from the display pixels 51 as described above, the living-body state can be easily detected and more information can be obtained based on the detection result of the living-body state. For example, if the pulsations of the heart of the user are detected as the living-body state, feelings or mental state of the user, for example, being nervous can be estimated.

Regarding the above-mentioned calibration processing, line-of-sight detection processing, and living-body state detection processing, all the processes are performed by the display apparatus 11. However, some processes may be performed by the control apparatus 81 shown in FIG. 7.

Second Embodiment

Figure 14:
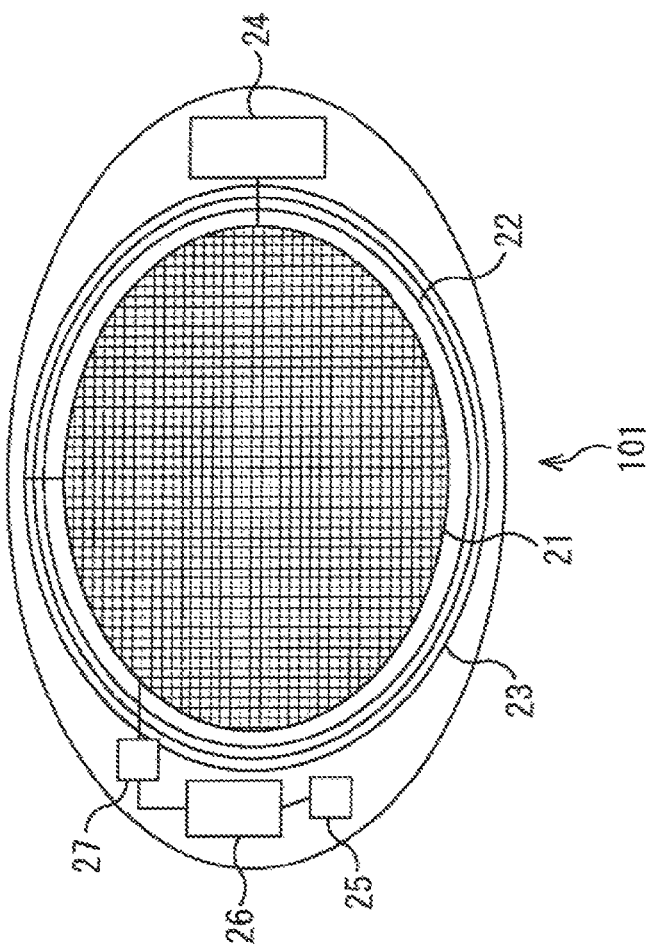
FIG. 14 A diagram showing of another configuration example of the display apparatus.

Configuration Example of Outer Appearance of Contact Lens Type Display Apparatus Furthermore, in the above, the example is which the shape as the display apparatus 11 is viewed from the front as shown in FIG. 2 is circular has been described, for example, as shown in FIG. 14, the shape may be oval. Note that, in FIG. 14, portions corresponding to those in FIG. 2 will be denoted by the same reference symbols and descriptions thereof will be appropriately omitted.

The display apparatus 101 shown in FIG. 14 is constituted of a display region 21, a feeding antenna 22, a signal antenna 23, a power generation unit 24, a sensor 25, a signal processing unit 26, and a display element drive unit 27.

The display region 21 to the display element drive unit 27 of the display apparatus 101 have the same configurations and operations as the display region 21 to the display element drive unit 27 of the display apparatus 11. Only the shape of the outer appearance of the entire apparatus and the shape of the display region 21 are different from the display apparatus 101 and the display apparatus 11.

FIG. 14 is a diagram as the display apparatus 101 is viewed in the same direction as that the user wearing the contact lens type display apparatus 101 is viewed from the front. In FIG. 14, the display apparatus 101 has an oval shape long in the lateral direction. Therefore, in the state in which the user wears the display apparatus 101 on the eyeball, in comparison with the circular display apparatus 11, it becomes difficult for the display apparatus 101 to rotate with respect to the eyeball. With this, rotation deviation of the display apparatus 101 with respect to the eyeball can be suppressed.

Furthermore, to the example in FIG. 14, the display region 21 of the display apparatus 101 has an oval shape long in the lateral direction.

In addition, the display apparatus 101 has a shape long in the lateral direction rather than the vertical direction in the figure, and hence a region of portions proximate in the left and right directions of the display region 21 has a larger area than a region of portions proximate in the upper and lower directions of the display region 21. These regions in the display apparatus 101 that are not the display regions 21 are regions outside the movement range of the pupil of the user.

In view of this, in the display apparatus 101, the power generation unit 24 to the display element drive unit 27 are arranged in the region near the left and right ends (lateral direction) of the display apparatus 101, which are proximate in the left and right directions of the display region 21 in the figure. By arranging elements for driving the display apparatus 101, such as the power generation unit 24 to the display element drive unit 27, in the left and right regions proximate in the left and right directions of the display region 21 in this manner, it is possible to prevent these elements from interrupting the image display.

Figure 15:
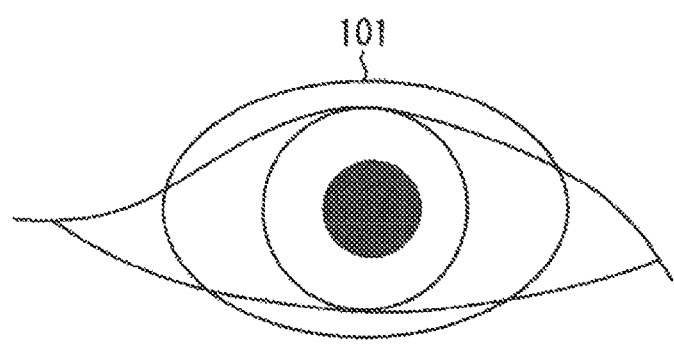
FIG. 15 A diagram showing a wearing state of the display apparatus.

FIG. 15 shows a wearing structure as the state in which the user wears the contact lens type display apparatus 101 is viewed from the front of the user.

The display apparatus 101 has a larger width in the lateral direction rather than the vertical direction in the figure. Therefore, in the state in which the display apparatus 101 is worn on the eyeball of the user, the lateral width is larger than the vertical width by which the display apparatus 101 covers the eyeball. Furthermore, the position of the end of the display apparatus 101 in the upper and lower directions is set to extend to the front of the connection between the eyelid and the eyeball of the user. The width in the left and right directions is set to be a width in a range in which the eyeball moves to the left and right. The width in the left and right directions is larger.

Furthermore, the display apparatus 101 has a structure in which it is fixed to the head such that the display apparatus 101 is not moved with respect to the head of the user.

For example, with respect to a movement of the eyeball due to variations in the line of sight of the user, when the contact lens type display apparatus 101 is moved together with the eyeball, an absolute position of information (image) currently displayed in the display region 21 with respect to the head of the user is also moved. The movement of the absolute position of the information (image) with respect to the head of the user is recognized as the movement of the display position. Therefore, it is desirable to constantly fix the position of the contact lens type display apparatus 101 with respect to the head of the user.

Figure 16:
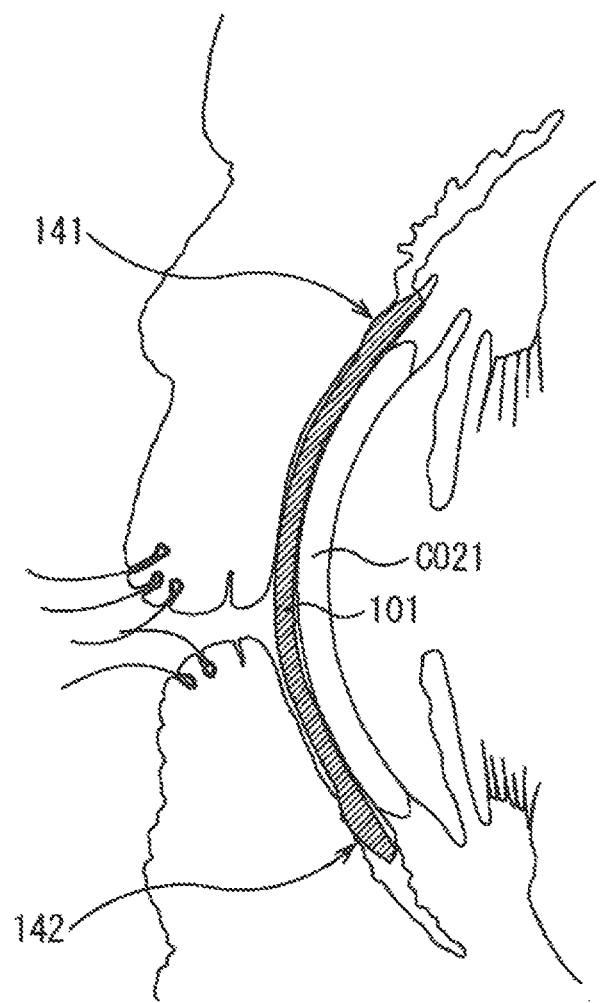
FIG. 16 A diagram for describing convex portions of the display apparatus.

In view of this, for example, as shown in FIG. 16, convex portions are provided near an outer circumference of the display apparatus 101. In the example shown in FIG. 16, the display apparatus 101 is worn to cover an entire cornea portion CO21 of the eyeball of the user.

Furthermore, in this example, the upper and lower ends of the display apparatus 101 are positioned in front of the connections at which the eyelid and the eyeball are connected to each other in the upper and lower ends, that is, near a limbus. In a surface on the external world side of the upper and lower end portions of the display apparatus 101, convex portion 141 and convex portion 142 protruding to the external world side are provided. The convex portion 141 and convex portion 142 are held in contact with the eyelid (palpebral conjunctiva). Thus, also when the eyeball moves or the user blinks, the display apparatus 101 is fixed not to be moved with respect to the head of the user.

Figure 17:
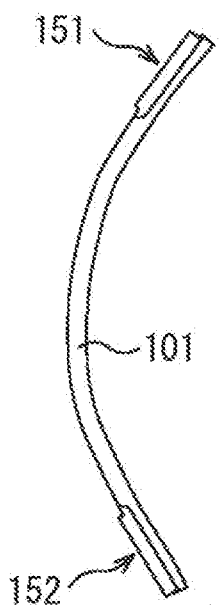
FIG. 17 A diagram for describing high-friction portions of the display apparatus.

The example in which the display apparatus 101 is provided with the convex portion 141 and the convex portion 142 has been described. However, for example, as shown in FIG. 17, by providing a high-friction portion 151 and a high-friction portion 152 near an upper and lower outer circumference of the display apparatus 101, the display apparatus 101 may be fixed with respect to the head of the user.

The high-friction portion 151 and the high-friction portion 152 are processed to have a higher coefficient of friction with respect to the eyelid in comparison with the center portion of the display apparatus 101. Therefore, in the state in which the display apparatus 101 is worn on the eyeball of the user, due to the friction of the high-friction portion 151 and high-friction portion 152 and the eyelid (palpebral conjunctiva) of the user, the display apparatus 101 is fixed not to be moved with respect to the head of the user.

Figure 18:
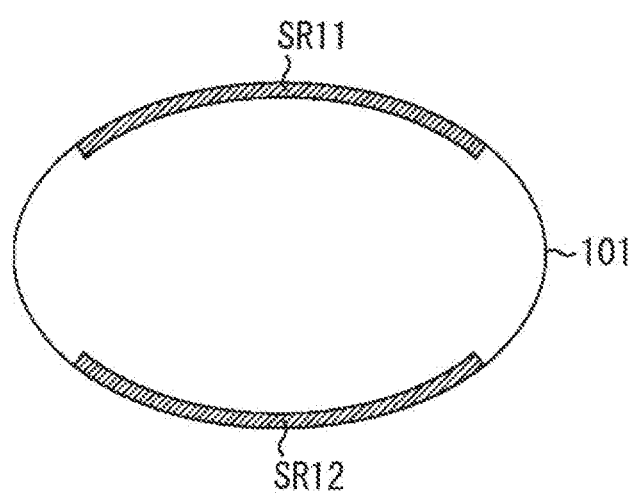
FIG. 18 A diagram for describing regions of the convex portions or high-friction portions of the display apparatus.

In this manner, if the display apparatus 101 is provided with the convex portion 141 and the convex portion 142 or the high-friction portion 151 and the high-friction portion 152, the convex portions and the high-friction portions are provided in region SR11 and region SR12 shown in FIG. 18.

Note that FIG. 18 is a diagram of the display apparatus 101 as the display apparatus 101 is viewed from the same direction as that when the user wearing the display apparatus 101 is viewed from the front. Therefore, an upper side in the figure of the display apparatus 101 corresponds to an upper side of the eye of the user and a lower side in the figure of the display apparatus 101 corresponds to a lower side of the eye of the user.

In this case, the convex portion 141 shown in FIG. 16 or the high-friction portion 151 shown in FIG. 17 is provided in the region SR11 formed along an upper end of the display apparatus 101. Furthermore, the convex portion 142 shown in FIG. 16 or the high-friction portion 152 shown in FIG. 17 is provided in the region SR12 formed along a lower end of the display apparatus 101.

Here, the convex portion 141 and the convex portion 142 or the high-friction portion 151 and the high-friction portion 152 are provided on a front side in the figure of the display apparatus 101, that is, the external world side.

The example in which the display apparatus 101 is provided with the convex portions and the high-friction portions has been described. However, the convex portions and the high-friction portions may be provided along upper and lower ends of the display apparatus 11 shown in FIG. 2.

Modified Example 1

Configuration Example of Display Region

The example in which the display pixels 51 and the light-receiving elements 52 are provided in a close contact state in the display region 21 as shown in FIG. 3 has been described above. However, the transmissive region for causing the ambient light from the outside to pass through the display region 21 may be provided.

Figure 19:
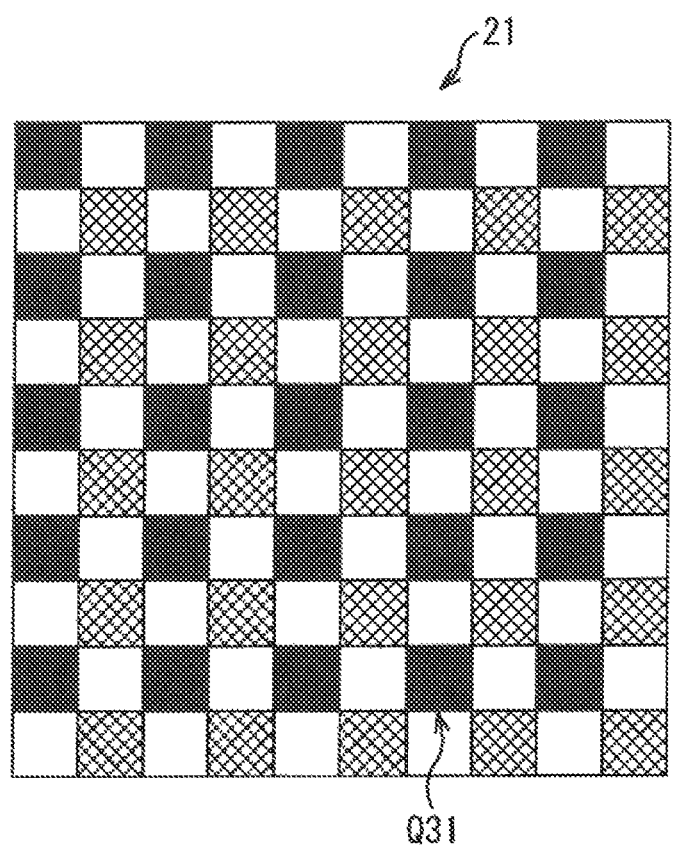
FIG. 19 A diagram showing another configuration example of the display region.

In such a case, the display region 21 is, for example, configured as shown in FIG. 19. Note that the vertical direction and the lateral direction in FIG. 19 correspond to, for example, the vertical direction and the lateral direction in FIG. 14. Furthermore, in FIG. 19, a single square region represents the display pixel 51, the light-receiving element 52, or the transmissive region.

Specifically, the black square represents a region of a single display pixel 51. The double-hatched square represents a region of a single light-receiving element 52. The white square represents a transmissive region. Here, the transmissive region is a region having a higher transmittance (transparency) against light in comparison with the display pixel 51 and the light-receiving element 52.

For example, a square indicated by an arrow mark Q31 represents a region of a single display pixel 51. The upper, lower, left, and right portions in the figure of the display pixels 51 are set as transmissive regions. Furthermore, in the obliquely upper and lower portions of the display pixel 51 indicated by the arrow mark Q31, the light-receiving element 52 is disposed. Therefore, each of the display pixels 51 is surrounded by four light-receiving elements 52 and four transmissive regions.

By providing the transmissive regions for causing light of the external world (ambient light) to pass through the display apparatus 11 or the display apparatus 101 around each display pixel 51 as described above, it becomes possible for the user to look around also when wearing the display apparatus 11 or the display apparatus 101. Furthermore, in this example, the light-receiving element 52 is disposed adjacent to each display pixel 51, and hence light output from the display pixel 51 and reflected by the eyeball can be received by the light-receiving element 52.

Modified Example 2

Configuration Example of Display Region

Figure 20:
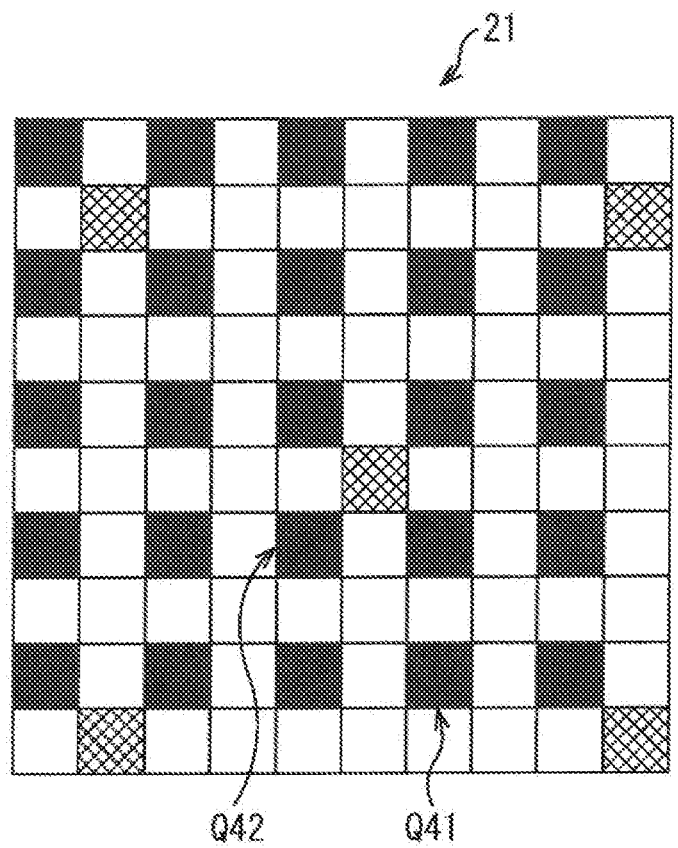
FIG. 20 A diagram showing another configuration example of the display region.

Furthermore, the display region 21 may be configured as shown if FIG. 20. Note that, in FIG. 20, the single square region represents the display pixel 51, the light-receiving element 52, or the transmissive region.

Specifically, the black square represents a region of a single display pixel 51. The double-hatched square represents a region of a single light-receiving 52. The white square represents a transmissive region.

For example, the square indicated by the arrow mark Q41 represents a region of a single display pixel 51 and the display pixel 51 is surrounded by the transmissive regions.

Furthermore, the square indicated by the arrow mark Q42 represents a region of a single display pixel 51. In an obliquely upper right portion in the figure of the display pixel 51, a single light-receiving element 52 is disposed. Other regions proximate to the display pixel 51 indicated by the arrow mark Q42 are transmissive regions.

In the example shown in FIG. 20, the number of light-receiving elements 52 provided in the display region 21 is smaller than the number of display pixels 51 provided in the display region 21. More transmissive regions are correspondingly provided. By providing light-receiving elements 52 fewer than the display pixels 51 as described above, it is possible to increase light (ambient light) passing through the display region 21 from the outside of the display apparatus. Further, the user can look around in a brighter view in comparison with the example shown in FIG. 19.

Modified Example 3

Configuration Example of Display Region

In addition, in the case where the display pixels 51 provided in the display region 21 have permeability, the user can look around through the display pixels 51 without providing the transmissive regions in the display region 21. In such a case, the display region 21 is, for example, configured as shown in FIG. 21.

Figure 21:
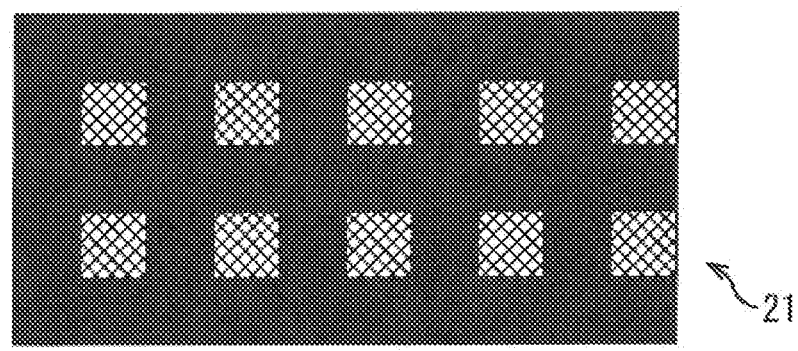
FIG. 21 A diagram showing another configuration example of the display region.

Note that, in FIG. 21, the black region represents a region of display pixels 51. The double-hatched square represents a region of a single light-receiving element 52.

In this example, the light-receiving elements 52 are disposed adjacent to the display pixels 51. Furthermore, the transmittance of light in the display pixel 51 is higher than the transmittance of light in the light-receiving element 52. The user can look around through the display pixels 51.

Third Embodiment

Configuration Example of Contact Lens Type Display Apparatus

Figure 22:
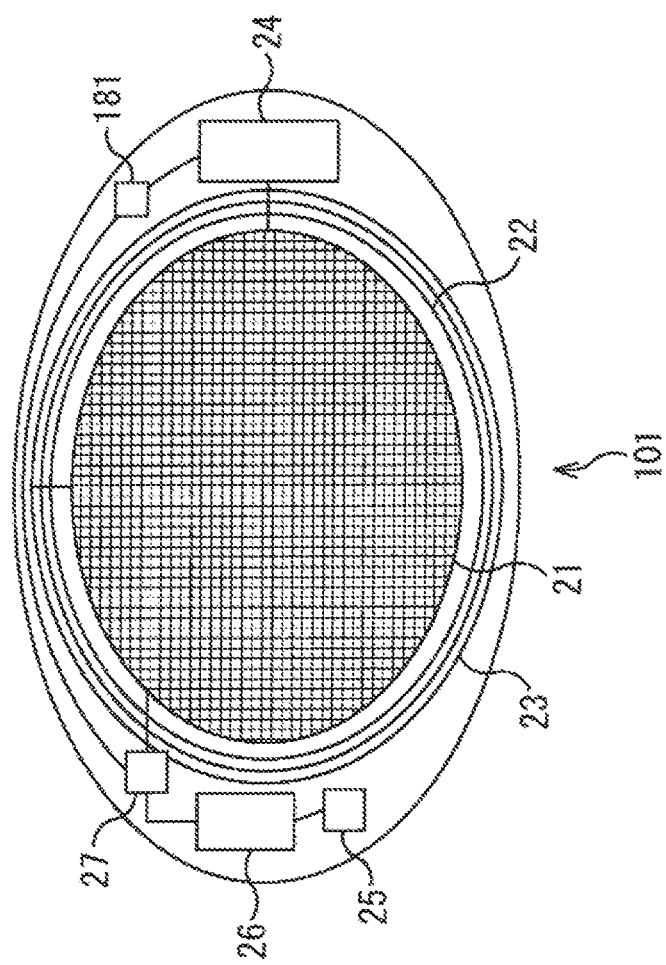
FIG. 22 A diagram showing another configuration example of the display apparatus.

In addition, a display apparatus 101 may be provided with the pressure sensor, the open/close of the eyelid of the user wearing the display apparatus 101 may be detected, and the pressure when the user strongly closes the eyelid may be detected. In such a case, the display apparatus 101 is, for example, configured as shown in FIG. 22. Note that, in FIG. 22, portions corresponding to those in FIG. 14 will be denoted by the same reference symbols and descriptions thereof will be appropriately omitted.

The display apparatus 101 shown in FIG. 22 is different from the display apparatus 101 in FIG. 14 in that the display apparatus 101 shown in FIG. 14 is further provided with a pressure sensor 181 but otherwise has the same configuration as the display apparatus 101 in FIG. 14.

That is, the display apparatus 101 in FIG. 22 is constituted of a display region 21, a feeding antenna 22, a signal antenna 23, a power generation unit 24, a sensor 25, a signal processing unit 26, a display element drive unit 27, and a pressure sensor 181.

The pressure sensor 181 is positioned near a right end in the figure and is operated by receiving electric power from the power generation unit 24. Furthermore, the pressure sensor 181 detects a pressure applied in a depth direction in the figure of the display apparatus 101 and supplies a detection result thereof to the signal processing unit 26 via the display element drive unit 27.

The signal processing unit 26 detects the close/open or the like of the eyelid of the user based on a detection result of the pressure supplied from the pressure sensor 181. For example, the signal processing unit 26 determines selection of the selection target when the user closes the eyelid or determines selection of the selection target when the user closes the eyelid, that is, a pressure higher than a predetermined value is detected.

By the pressure sensor 101 detecting the user's operation based on the detection result of the pressure in this manner, it is possible to further enhance the operability of the display apparatus 101.

Fourth Embodiments

Configuration Example of Contact Lens Type Line-of-Sight Detection Apparatus

Note that the example at which the present technology of detecting the user's line-of-sight direction is applied to the display apparatus has been described above. The present technology is not limited to the display apparatus. The present technology is applicable to all apparatuses that detects the user's line-of-sight direction (eyeball direction). Hereinafter, an embodiment in which the present technology is applied to the line-of-sight detection apparatus that detects the user's line-of-sight direction will be described.

Figure 23:
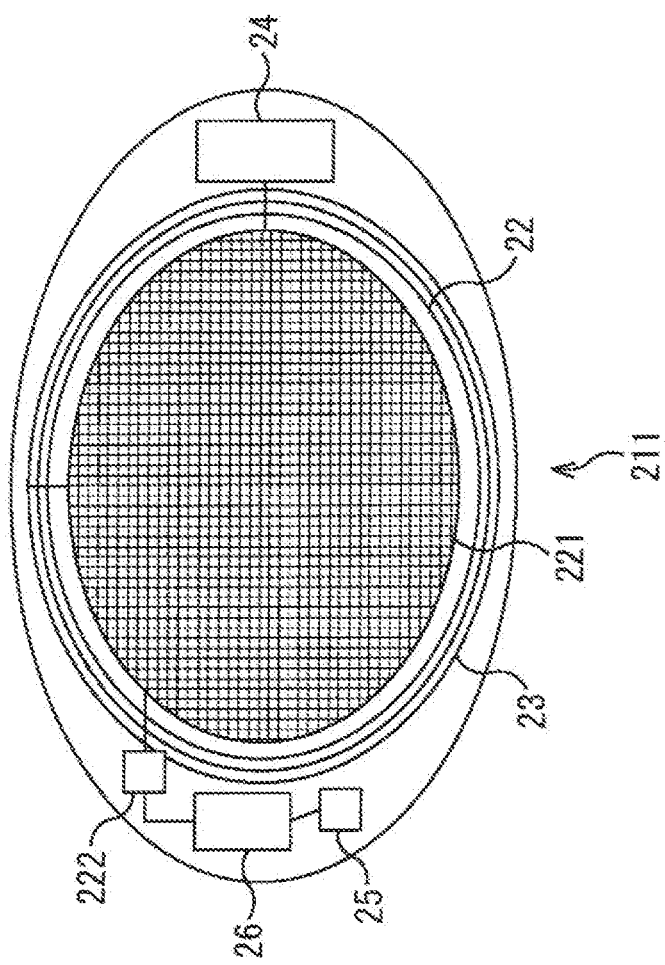
FIG. 23 A diagram showing a configuration example of a line-of-sight detection apparatus.

FIG. 23 is a diagram showing a configuration example of a line-of-sight detection apparatus to which the present technology is applied. Note that, in FIG. 23, portions corresponding to those in FIG. 2 will be denoted by the same reference symbols and descriptions thereof will be appropriately omitted.

A contact lens type line-of-sight detection apparatus 211 has a shape such that it can be worn on the eyeball of the user. In the state in which a line-of-sight detection apparatus 211 is worn on the eyeball, the line-of-sight detection apparatus 211 covers the entire cornea portion of the eyeball of the user.

The line-of-sight detection apparatus 211 is constituted of a detection region 221, a feeding antenna 22, a signal antenna 23, a power generation unit 24, a sensor 25, a signal processing unit 26, and a light-emitting element drive unit 222.

Note that FIG. 23 is a diagram of the line-of-sight detection apparatus 211 as the line-of-sight detection apparatus 211 is viewed from the same direction as that when the user wearing the line-of-sight detection apparatus 211 is viewed from the front. In FIG. 23, the line-of-sight detection apparatus 211 has an oval shape.

The detection region 221 includes a light-emitting element formed of a plurality of light-emitting sections that emit light for the line-of-sight detection to the eyeball surface of the user and a light-receiving element that is disposed adjacent to the light-emitting sections and receives light reflected by the eyeball surface of the user. Furthermore, as in the above-mentioned display region 21, in the detection region 221 at least one of the light-emitting section and the light-receiving element are provided in a region in the detection region 221 that is opposed to a region in a range in which the pupil of the eyeball of the user is movable.

The light-emitting element drive unit 222 drives the light-emitting element of the detection region 221 under the control of the signal processing unit 26, emits light from each light-emitting section, and supplies the light-receiving signals supplied from the light-receiving elements of the detection region 221 to the signal processing unit 26.

In the line-of-sight detection apparatus 211, the positions of the feeding antenna 22 to the signal processing unit 26 are the same positions as in the case of the display apparatus 101 in FIG. 14.

Figure 24:
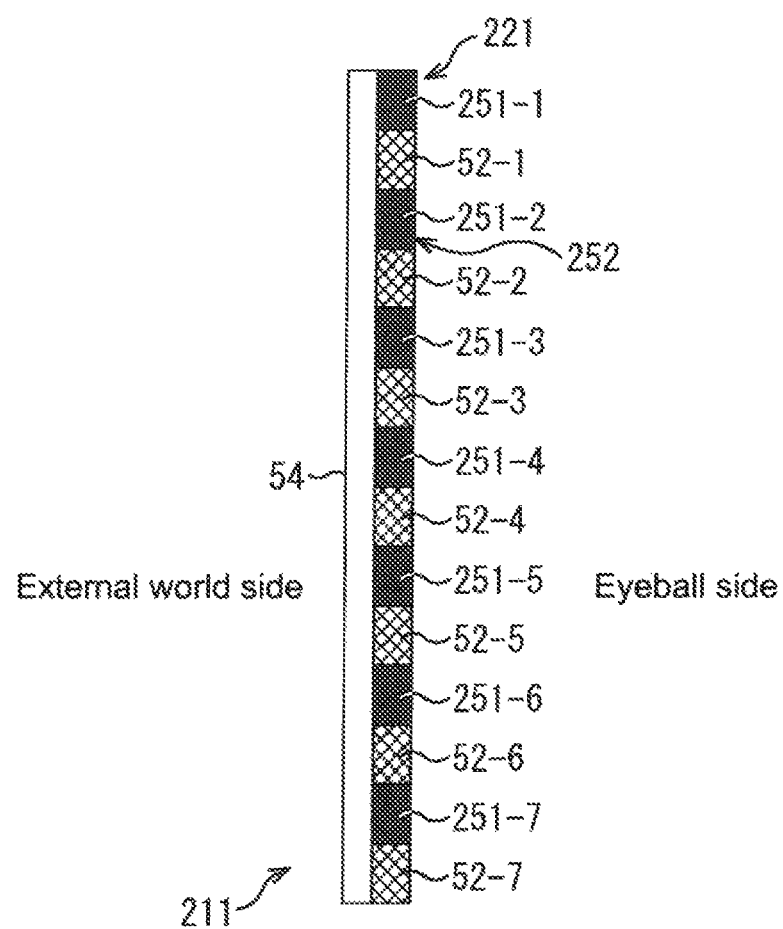
FIG. 24 A diagram showing a configuration example of a detection region.

Furthermore, the detection region 221 of the line-of-sight detection apparatus 211 is, for example, configured as shown in FIG. 24. Note that FIG. 24 shows a part of a cross-section of the line-of-sight detection apparatus 211 as the line-of-sight detection apparatus 211 is viewed from the lateral direction in FIG. 23. Note that, in FIG. 24, portions corresponding to those in FIG. 3 will be denoted by the same reference symbols and descriptions thereof will be appropriately omitted.

In FIG. 24, in the detection region 221 of the line-of-sight detection apparatus 211, the light-emitting sections 251-1 to 251-7 that emit light for detecting the line-of-sight direction and the light-receiving elements 52-1 to 52-7 that receive reflected light entering the eyeball surface of the user are provided. Then, a single light-emitting device formed of the light-emitting sections 251-1 to 251-7 is set as a light-emitting element 252.

Hereinafter, in the case where the light-emitting sections 251-1 to 251-7 do not need to be particularly distinguished from one another, they will be also simply referred to as light-emitting sections 251.

The light-emitting section 251 has a function of emitting light for line-of-sight detection by emitting light. However, the light-emitting section 251 has a function of displaying information as in the display pixels 51 shown in FIG. 3.

In the example in FIG. 24, the light-emitting sections 251 and the light-receiving elements 52 are alternately arranged on the right side in the figure of the line-of-sight detection apparatus 211, that is, on the side of the eyeball of the user in the vertical direction. Therefore, for example, in FIG. 23, the light-emitting sections 251 and the light-receiving elements 52 are alternately arranged in the vertical direction and the lateral direction in FIG. 23 in the detection region 22.

Note that, in FIG. 24, the example in which the light-emitting sections 251 and the light-receiving elements 52 are in close contact has been described. The light-emitting sections 251 and the light-receiving elements 52 do not necessarily need to be in close contact. A clearance between the light-emitting sections 251 and the light-receiving elements 52 may be provided. Furthermore, in FIG. 24, one light-receiving element 52 is provided for one light-emitting section 251. However, one light-receiving element 52 may be provided for a plurality of light-emitting sections 251.

In addition, the example in which the light-emitting element 252 formed of the plurality of light-emitting sections 251 is provided in the detection region 221 has been described. However, the light-emitting element 252 formed of a single light-emitting section that emits light in the entire region of the detection region 221 may be provided in the detection region 221. In this case, in each region of the light-emitting element 252, the light-receiving elements 52 for detecting the light-receiving amounts in these regions only need to be provided.

Furthermore, in the case where only light entering the eyeball from the external world is used to detect the user's line-of-sight direction, it is not necessarily necessary to provide the line-of-sight detection apparatus 211 with the light-emitting element 252.

Description of Calibration Processing

Next, operations of the line-of-sight detection apparatus 211 will be described.

Figure 25:
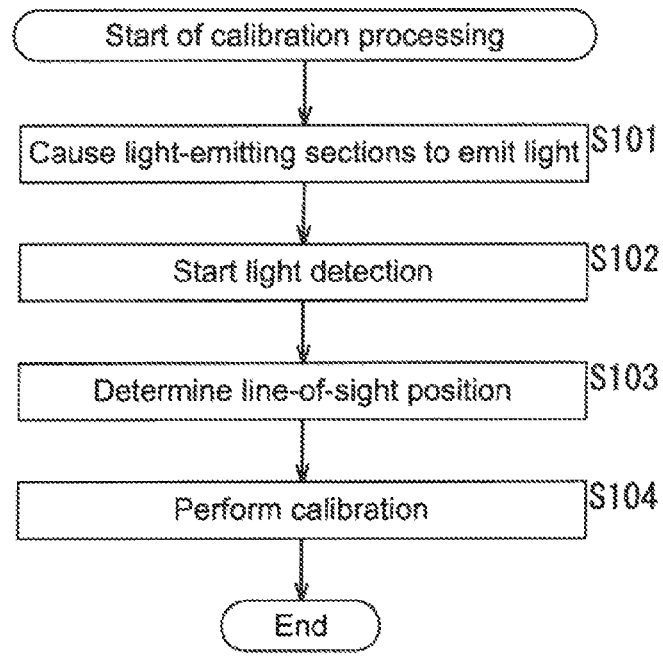
FIG. 25 A flowchart for describing calibration processing.

For example, when the line-of-sight detection apparatus 211 is worn by the user, the calibration processing is started. Hereinafter, the calibration processing by the line-of-sight detection apparatus 251 will be described with reference to a flowchart in FIG. 25.

In Step S101, the signal processing unit 26 controls the light-emitting element drive unit 222 to cause the light-emitting sections 251 to emit light. The light-emitting sections 251 emit light under the control of the light-emitting element drive unit 222 and outputs light for detecting the user's line-of-sight direction.

In Step S102, the light-receiving elements 52 start defection of light entering from the eyeball. That is, the light-receiving elements 52 receive light that has entered the eyeball from the outside of the line-of-sight detection apparatus 211 or the light-emitting sections 251 and been reflected by the eyeball surface perform photoelectric conversion, and supply light-receiving signals according to light-receiving amounts to the signal processing unit 26 via the light-emitting element drive unit 222.

Furthermore, when the calibration processing is started, the user looks in a direction set in advance. For example, according to a sound guidance or the like output from the control apparatus wirelessly connected to the line-of-sight detection apparatus 211, the user moves the line of sight in the upper, lower, left, or right direction as largely as possible.

While the user moves the line of sight in the upper, lower, left, or right direction as described above, light for detecting the line-of-sight direction is output from the light-emitting sections 251. The light-receiving elements 52 receive light entering from the eyeball surface, for example, light that has been output from the light-emitting sections 251 and reflected by the eyeball. Then, the light-receiving elements 52 supply light-receiving signals according to light-receiving amounts to the signal processing unit 26 via the light-emitting element drive unit 222.

In Step S103, the signal processing unit 26 determines a user's line-of-sight position based on the light-receiving signals supplied from the light-receiving elements 52.

For example, when the user largely moves the line of sight in the upper, lower, left, or right direction, the signal processing unit 26 determines a position of each of upper, lower, left, and right ends of the line of sight moved by the user as a line-of-sight position. With this, the user can determine a range in which the line of sight is movable based on the line-of-sight positions. Note that, during calculation of the line-of-sight position, for example, the same processing as Step S14 in FIG. 11 is performed.

In Step S104, the signal processing unit 26 performs calibration based on the determined line-of-sight position and the calibration processing ends.

For example, it is assumed that, after calibration, the detection result of the line of sight by the line-of-sight detection apparatus 211 is used for processing of moving a cursor on an external display different from the line-of-sight detection apparatus 211 by the user moving the line of sight.

In such a case, the signal processing unit 26 determines a range in which the line of sight of the user is movable based on the line-of-sight position with respect to each of the upper, lower, left and right positions, which is determined in the processing of Step S103. Then, the signal processing unit 26 performs calibration by making each position of the region, which is obtained by subtracting a margin from the range in which the line of sight of the user is movable, corresponding to each position of the display.

In the above-mentioned manner, the line-of-sight detection apparatus 211 performs calibration based on some line-of-sight positions. By performing calibration in this manner, it is possible to obtain a correspondence or the like of a particular region of the external display or the like and a region as a moving destination of the line of sight of the user, and hence to enhance the operability of the interface operation performed by the user.

Description of Line-of-Sight Detection Processing

For example, in the case where the line-of-sight detection apparatus 211 and the external control apparatus are wirelessly connected to each other, when the calibration processing is performed, the user can activate an arbitrary application program and execute desired processing.

For example, during execution of the application program, the user can move the line of sight and perform various operations. In such a case, the line-of-sight detection apparatus 211 performs line-of-sight detection processing to detect the user's line-of-sight position and outputs a detection result thereof to the external control apparatus.

Figure 26:
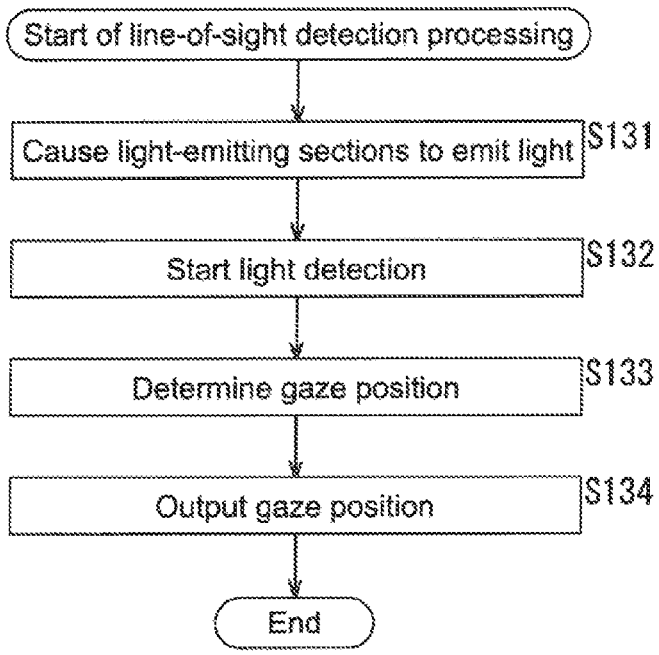
FIG. 26 A flowchart for describing line-of-sight detection processing.

Hereinafter, line-of-sight detection processing by the line-of-sight detection apparatus 211 will be described with reference to a flowchart in FIG. 26.

In Step S131, the signal processing unit 26 controls the light-emitting element drive unit 222 to cause the light-emitting sections 251 to emit light. The light-emitting sections 251 emit light under the control of the light-emitting element drive unit 222 and output light for detecting the user's line-of-sight direction.

In Step S132, the light-receiving elements 52 start detection of light entering from the eyeball. That is, the light-receiving elements 52 receive light that has entered from the outside of the line-of-sight detection apparatus 211 or the light-emitting sections 251 and been reflected by the eyeball surface, perform photoelectric conversion, and supply light-receiving signals according to light-receiving amounts to the signal processing unit 26 via the light-emitting element drive unit 222.

In Step S133, the signal processing unit 26 determines a user's line-of-sight position based on the light-receiving signals supplied from the light-receiving elements 52. That is, the signal processing unit 26 generates a light-receiving signal map based on the light-receiving signals and determines a user's line-of-sight position by detecting a pupil center (eyeball direction) of the user based on the obtained light-receiving signal map.

In Step S134, the signal processing unit 26 outputs the determined line-of-sight position and terminates the line-of-sight detection processing.

For example, the signal processing unit 26 supplies the determined line-of-sight position to the signal antenna 23 and causes the control apparatus to send it. The control apparatus executes processing according to the line-of-sight position, for example, moving the cursor or the like according to the line-of-sight position received from, for example, the line-of-sight detection apparatus 211.

In the above-mentioned manner, in the line-of-sight detection apparatus 211, light from the light-emitting sections 251 or the like is received by the light-receiving elements 52. The line-of-sight position is detected based on the obtained light-receiving signals. A detection result thereof is output.

By detecting the line-of-sight position based on the light-receiving signals obtained by the light-receiving elements 52 in this manner, it is possible to easily determine the user's operation without needing the external apparatus other than the line-of-sight detection apparatus 211. In other words, it is possible to enhance the operability with a simple configuration.

Here, the processing in which the line-of-sight detection apparatus 211 detects the user's line-of-sight position has been described. However, the line-of-sight detection apparatus 211 may cause the light-emitting sections 251 to output light having a particular wavelength from the light-emitting sections 251 for detecting the living-body state, calculating a convergence amount of the left and right eyes or a distance to a target object, or determining a diameter of the pupil.

In addition, in the above, the example in which, using the feet that the value of the light-receiving signal in the pupil region in the light-receiving signal map is smaller than the value of the light-receiving signal in the region of the sclera or iris portion, the pupil region, that is, the line-of-sight position is detected based on the light-receiving signal map has been described.

In other words, using a difference between a spectral reflectance of the retina at which light transmitted through the pupil arrives and a spectral reflectance of the sclera or iris portion, the pupil region of the user is detected based on the light-receiving signal map.

Therefore, depending on the wavelength of light emitted from the display pixels 51, the light-emitting sections 251, or the like, the reflectance of the retina is in some cases higher than the reflectance of the sclera or iris portions. In those cases, in the light-receiving signal map, the value of the light-receiving signal in the pupil region is higher than the value of the light-receiving signal in the region of the sclera or iris portion.

Also in the case where light by which the reflectance of the retina is higher than the reflectance of the sclera or iris portion is output from the display pixels 51 or the light-emitting sections 251 as described above, it is possible to detect the pupil region based on the light-receiving signal map in the signal processing unit 26. In this case, the signal processing unit 26 detects a region of the light-receiving signal map, in which the value of the light-receiving signal is high, as the pupil region.

In any case, the signal processing unit 26 is capable of detecting the pupil region (line-of-sight position) based on the value of the light-receiving signal in each region of the light-receiving signal map. At this time, whether to set the region in which the value of the light-receiving signal is high or the region in which the value of the light-receiving signal is low as the pupil region only needs to be determined depending on the wavelength of the light output from the display pixels 51 or the light-emitting sections 251, the spectral reflectance properties of the sclera, iris, and retina, and the like.

Note that embodiments of the present technology are not limited to the above-mentioned embodiments and various modifications can be made without departing from the gist of the present technology.

For example, the present technology can take a cloud computing configuration in which a single function is shared with a plurality of apparatuses over a network and commonly processed.

Furthermore, the steps described with reference to the flowcharts above can be executed by a single apparatus and can be otherwise shared with and executed by a plurality of apparatuses.

In addition, in the case where a single step includes a plurality of processes, the plurality of processes included in the single step can be executed by the single apparatus and can be otherwise shared with and executed by the plurality of apparatuses.

In addition, the present technology may also take the following configurations.

[1]
A detection apparatus that is wearable on an eyeball, including
a light-receiving element that receives light entering from the eyeball.

[2]
The detection apparatus according to [1], further including
a light-emitting element that outputs light, in which
the light-receiving element is provided near the light-emitting element.

[3]
The detection apparatus according to [2], in which
the light-emitting element is formed of a plurality of light-emitting sections, and
the light-receiving element is provided near the light-emitting section.

[4]
The detection apparatus according to [3], in which
the light-receiving element receives light that is output from the light-emitting section and reflected by the eyeball
further including
a signal processing unit that detects light-receiving amounts of a plurality of light-receiving elements arranged in regions of the detection apparatus.

[5]
The detection apparatus according to [3] or [4], in which
the light-emitting section is a display pixel that displays information.

[6]
The detection apparatus according to any one of [2] to [5], in which
the detection apparatus is configured to cover an entire cornea portion when the detection apparatus is worn on the eyeball.

[7]
The detection apparatus according to any one of [3] to [6], in which
in a state in which the detection apparatus is worn on the eyeball, at least one of the light-emitting section and the light-receiving element is provided in a region of the detection apparatus that is opposed to a region in a range in which a pupil of the eyeball is movable.

[8]
The detection apparatus according to any one of [2] to [7], in which
a lateral width is set to be larger than a vertical width by which the detection apparatus covers the eyeball.

[9]
The detection apparatus according to [8], in which
an element different from the light-emitting element and the light-receiving element is provided near a lateral end of the detection apparatus.

[10]
The detection apparatus according to [2] to [9], in which
the detection apparatus has a structure for fixing the detection apparatus with respect to a head having the eyeball.

[11]
The detection apparatus according to [4], in which
the signal processing unit determines a direction of the eyeball based on the light-receiving amounts of the plurality of light-receiving elements.

[12]
The detection apparatus according to [11], in which
the signal processing unit calculates a convergence amount of left and right eyes based on the direction of the eyeball and a direction of an eyeball that pairs with the eyeball and calculates a distance to a gazed target object based on the convergence amount.

[13]
The detection apparatus according to [4], in which
the signal processing unit determines a diameter of a pupil of the eyeball based on the light-receiving amounts of the plurality of light-receiving elements.

[14]
The detection apparatus according to [4], in which
the signal processing unit detects a living-body state based on the light-receiving amounts of the plurality of light-receiving elements.

[15]
The detection apparatus according to [14], in which
the light-emitting section emits light having a predetermined wavelength to the eyeball or emits light having different wavelengths to the eyeball in order, and
the signal processing unit detects the living-body state based on light-receiving amounts of the light having the predetermined wavelength or the light having the different wavelengths that is emitted to the eyeball, in the light-receiving elements.

[16]
The detection apparatus according to [15], in which
the light-emitting section is a display pixel that displays information and emits, after a period in which the information is displayed, the light having the predetermined wavelength or the light having the different wavelengths to the eyeball.

[17]
A detection method for a detection apparatus including
a light-receiving element that receives light entering from an eyeball, and
a signal processing unit that detects a light-receiving amount of the light-receiving element and being wearable on the eyeball, the method including:
a light-receiving step of receiving, by the light-receiving element, light reflected by the eyeball; and
a detection step of detecting, by the signal processing unit, light-receiving amounts of a plurality of light-receiving elements arranged in regions of the detection apparatus.

[18]
The detection method according to [17], further including
a light-emitting step of outputting light by a light-emitting element provided in the detection apparatus, in which
the light-receiving element receives, in the light-receiving step, light output from the light-emitting element and reflected by the eyeball.

[19]
The detection method according to [18], further including
a calculation step of determining, by the signal processing unit, a direction of the eyeball based on the light-receiving amounts of the plurality of light-receiving elements.

[20]
The detection method according to [19], is which
the signal processing unit calculates, in the calculation step, a convergence amount of left and right eyes based on the direction of the eyeball and a direction of an eyeball that pairs with the eyeball and calculates a distance to a gazed target object based on the convergence amount.

DESCRIPTION OF REFERENCE NUMERALS 11 display apparatus
21 display region
23 signal antenna
25 sensor
26 signal processing unit
27 display element drive unit
51-1 to 51-7, 51 display pixel.
52-1 to 52-7, 52 light-receiving element
53 display element
81 control apparatus
101 display apparatus
141 convex portion
142 convex portion
151 high-friction ports on
1.52 high-friction portion
181 pressure sensor
2.1 line of sight detection apparatus
251-1 to 251-7, 251 light-emitting section
252 light-emitting element

The invention claimed is:

1. A detection apparatus, comprising:
   a display region;
   a light-emitting element configured to output light, wherein the light-emitting element includes a plurality of light-emitting sections; and
   a plurality of light-receiving elements configured to receive light that enters from a first eyeball of a user,
   wherein the plurality of light-receiving elements and the plurality of light-emitting sections are at alternate positions on an entire surface of the display region, and
   wherein the detection apparatus is wearable on the first eyeball of the user.

2. The detection apparatus according to claim 1, further comprising
   a signal processing unit configured to detect a light-receiving amount of each of the plurality of light-receiving elements,
   wherein the plurality of light-receiving elements are configured to receive light that is output from the plurality of light-emitting sections and reflected by the first eyeball.

3. The detection apparatus according to claim 1, wherein a structure of the detection apparatus is configured to fix the detection apparatus with respect to a head of the user.

4. The detection apparatus according to claim 2, wherein the signal processing unit is further configured to determine a first direction of the first eyeball based on the light-receiving amount of each of the plurality of light-receiving elements.

5. The detection apparatus according to claim 4, wherein the signal processing unit is further configured to:
   calculate a convergence amount of left and right eyes of the user based on the first direction of the first eyeball and a second direction of a second eyeball of the user that pairs with the first eyeball; and
   determine a distance to a gazed target object based on the convergence amount.

6. The detection apparatus according to claim 2, wherein the signal processing unit is further configured to determine a diameter of a pupil of the first eyeball based on the light-receiving amount of each of the plurality of light-receiving elements.

7. The detection apparatus according to claim 2, wherein the signal processing unit is further configured to detect a living-body state of the user based on the light-receiving amount of each of the plurality of light-receiving elements.

8. The detection apparatus according to claim 7, wherein
   each of the plurality light-emitting sections is configured to emit, to the first eyeball, light having one of a determined wavelength or different wavelengths, and
   the signal processing unit is further configured to detect the living-body state based on the light-receiving amount of the light having one of the determined wavelength or the different wavelengths.

9. The detection apparatus according to claim 8, wherein each of the plurality of light-emitting sections is a display pixel that displays information and emits, after a period in which the information is displayed, the light having one of the determined wavelength or the different wavelengths to the first eyeball.

10. The detection apparatus according to claim 1, wherein each of the plurality of light-emitting sections is a display pixel that displays information.

11. The detection apparatus according to claim 1, wherein the detection apparatus is configured to cover an entire cornea portion based on the detection apparatus that is worn on the first eyeball.

12. The detection apparatus according to claim 1, wherein the display region is opposed to a pupil of the first eyeball.

13. The detection apparatus according to claim 1, wherein the detection apparatus is configured to cover the first eyeball and wherein a lateral width of the detection apparatus is set to be larger than a vertical width of the detection apparatus.

14. The detection apparatus according to claim 13, further comprising a sensor different from the light-emitting element and the plurality of light-receiving elements, and wherein the sensor is at a determined proximity from a lateral end of the detection apparatus.

15. The detection apparatus according to claim 14, wherein the sensor is one of a gyro sensor or a gravity sensor.

16. A detection method, comprising:
   in a detection apparatus including a display region, a plurality of light-receiving elements, a light-emitting element that includes a plurality of light-emitting sections, and a signal processing unit:
   outputting light by the plurality of light-emitting sections;
   receiving, by the plurality of light-receiving elements, light entering from a first eyeball of a user; and
   detecting, by the signal processing unit, a light-receiving amount of each of the plurality of light-receiving elements,
   wherein the plurality of light-receiving elements and the plurality of light-emitting sections are at alternate positions on an entire surface of the display region, and
   wherein the detection apparatus is wearable on the first eyeball of the user.

17. The detection method according to claim 16, further comprising
   receiving, by the plurality of light-receiving elements, light output from the light-emitting element and reflected by the first eyeball.

18. The detection method according to claim 17, further comprising determining, by the signal processing unit, a first direction of the first eyeball based on the light-receiving amount of each of the plurality of light-receiving elements.

19. The detection method according to claim 18, further comprising:
- calculating a convergence amount of left and right eyes based on the first direction of the first eyeball and a second direction of a second eyeball of the user that pairs with the first eyeball; and
- determining a distance to a gazed target object based on the convergence amount.

* * * * *